(12) United States Patent
Hill et al.

(10) Patent No.: US 7,218,964 B2
(45) Date of Patent: May 15, 2007

(54) CLOSED-LOOP NEUROMODULATION FOR PREVENTION AND TREATMENT OF CARDIAC CONDITIONS

(75) Inventors: Michael R. S. Hill, Minneapolis, MN (US); Gary W. King, Fridley, MN (US); Thomas J. Mullen, Ham Lake, MN (US); Xiaohong Zhou, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 474 days.

(21) Appl. No.: 10/035,319

(22) Filed: Oct. 26, 2001

(65) Prior Publication Data

US 2002/0165586 A1 Nov. 7, 2002

Related U.S. Application Data

(60) Provisional application No. 60/294,072, filed on May 29, 2001, provisional application No. 60/243,393, filed on Oct. 26, 2000, provisional application No. 60/243,536, filed on Oct. 26, 2000, provisional application No. 60/243,609, filed on Oct. 26, 2000.

(51) Int. Cl.
  *A61N 1/372* (2006.01)
(52) U.S. Cl. .......................................................... 607/9
(58) Field of Classification Search ................ 600/373, 600/374, 382, 509, 513, 515, 518, 519, 521; 607/4–7, 9, 14, 17, 44, 117, 118, 119, 120, 607/122
See application file for complete search history.

(56) References Cited

U.S. PATENT DOCUMENTS

| | | | |
|---|---|---|---|
| 3,421,511 A | 1/1969 | Schwartz et al. | |
| 3,522,811 A | 8/1970 | Seymour et al. | 128/419 |
| 3,593,718 A * | 7/1971 | Krasner et al. | 607/20 |
| 3,645,267 A | 2/1972 | Hagfors | 128/421 |
| 3,650,277 A | 3/1972 | Sjostrand et al. | 128/419 C |
| 3,796,221 A | 3/1974 | Hagfors | 128/421 |
| 4,044,774 A | 8/1977 | Corbin et al. | 128/404 |
| 4,146,029 A | 3/1979 | Ellinwood, Jr. | 128/260 |
| 4,340,063 A | 7/1982 | Maurer | 128/421 |

(Continued)

FOREIGN PATENT DOCUMENTS

EP 0 688 577 12/1995

OTHER PUBLICATIONS

Braunwald, M.D. et al, Carotid Sinus Nerve Stimulation in the Treatment of Angina Pectoris and Supraventricular Tachycardia.

(Continued)

*Primary Examiner*—Robert E. Pezzuto
*Assistant Examiner*—Frances P. Oropeza
(74) *Attorney, Agent, or Firm*—Paul H. McDowall; Girma Wolde-Michael

(57) ABSTRACT

A method and apparatus to provide therapy to a patient for protecting cardiac tissue from insult is disclosed. The method comprises delivering closed loop electrical stimulation to one or more predetermined portions of a portion of excitable tissue of the spinal cord of a patient; and monitoring one or more physiologic indices of the body. That is, a closed-loop feedback controller is used to apply electrical stimulation to preselected regions of the spinal cord of a patient's body based upon one or more aspects of the physiologic indices.

17 Claims, 13 Drawing Sheets

U.S. PATENT DOCUMENTS

| | | | |
|---|---|---|---|
| 4,428,378 A | 1/1984 | Anderson et al. | 128/419 |
| 4,458,696 A | 7/1984 | Larimore | |
| 4,549,556 A | 10/1985 | Tarjan et al. | 128/785 |
| 4,694,835 A | 9/1987 | Strand | |
| 4,903,701 A | 2/1990 | Moore et al. | 128/419 |
| 5,031,618 A | 7/1991 | Mullett | 128/421 |
| 5,058,584 A | 10/1991 | Bourgeois | 128/421 |
| 5,135,004 A | 8/1992 | Adams et al. | 128/696 |
| 5,149,713 A | 9/1992 | Bousquet | |
| 5,199,428 A | 4/1993 | Obel et al. | 128/419 |
| 5,203,326 A | 4/1993 | Collins | |
| 5,220,917 A * | 6/1993 | Cammilli et al. | 607/122 |
| 5,255,691 A | 10/1993 | Otten | 607/117 |
| 5,292,336 A | 3/1994 | Spence, Jr. et al. | |
| 5,292,338 A | 3/1994 | Bardy | |
| 5,330,505 A | 7/1994 | Cohen | 607/6 |
| 5,330,507 A | 7/1994 | Schwartz | 607/14 |
| 5,330,515 A | 7/1994 | Rutecki et al. | 607/46 |
| 5,331,966 A | 7/1994 | Bennett et al. | 128/696 |
| 5,331,996 A | 7/1994 | Ziehm | |
| 5,342,409 A | 8/1994 | Mullett | 607/46 |
| 5,360,441 A | 11/1994 | Otten | 607/122 |
| 5,464,434 A | 11/1995 | Alt | 607/6 |
| 5,496,363 A | 3/1996 | Burgio et al. | |
| 5,564,434 A | 10/1996 | Halperin et al. | 128/48 |
| 5,607,418 A | 3/1997 | Arzbaecher | 604/891 |
| 5,700,282 A | 12/1997 | Zabara | |
| 5,792,187 A | 8/1998 | Adams | |
| 5,817,131 A | 10/1998 | Elsberry et al. | 607/5 |
| 5,824,021 A | 10/1998 | Rise | 607/46 |
| 6,006,134 A | 12/1999 | Hill et al. | |
| 6,058,331 A | 5/2000 | King | 607/62 |
| 6,073,048 A | 6/2000 | Kieval et al. | |
| 6,134,470 A | 10/2000 | Hartlaub | 607/14 |
| 6,178,349 B1 | 1/2001 | Kieval | |
| 6,272,377 B1 * | 8/2001 | Sweeney et al. | 600/515 |

OTHER PUBLICATIONS

Bilgutay, M.D. et al, Vagal Tuning—A New Concept in the Treatment of Supraventricular Arrhythmias, Angina Pectoris, and Heart Failure, Journal of Thorac Cardiovascular Surgery 56 (1): 71-82, Jul. 1968.

Foreman et al, Modulation of Intrinsic Cardiac Neurons by Spinal Cord Stimulation: Implications for its Therapeutic Use in Angina Pectoris, Cardiovascular Research 47, pp. 367-375, Apr. 10, 2000.

Bilgutay, et al., "Vagal Tuning, " from *Journal of Thoracic & Cardiovascular Surgery*, Jul. 1968, 56:71-82.

Braunwald, et al., "Carotid Sinus Nerve Stimulation in the Treatment of Angina Pectoris and Supraventricular Tachycardia," from *California Medicine, The Western Journal of Medicine*, Mar. 1970, 112(3):41-50.

Armour, "Instant-to-Instant Reflex Cardiac Regulation," 1976, 309-328.

Schwartz, et al., "Effect of dorsal root section on the arrhythmias associated with coronary occlusion," from *American Journal of Physiology*, Sep. 1976, pp. 923-928.

Blair, et al., "Responses of Thoracic Spinothalamic Neurons to Intracardiac Injection of Bradykinin in the Monkey," from *Circulation Research* vol. 51, No. 1, Jul. 1982, pp. 83-94.

Ammons, et al., "Vagal Afferent Inhibition of Spinothalamic Cell Responses to Sympathetic Afferents and Bradykinin in the Monkey," from *Circulation Research*, vol. 53, No. 5, Nov. 1983, pp. 603-612.

Blair, et al., "Responses of Thoracic Spinothalamic and Spinoreticular Cells to Coronary Artery Occlusion," from *Journal of Neurophysiology*, vol. 51, No. 4, Apr. 1984, pp. 636-648.

Ammons, et al., "Effects of intracardiac bradykinin on $T_2$—$T_5$ medial spinothalamic cells," from *American Journal of Physiology*, 1985, pp. R147-R152.

Blair, et al., "Activation Of Feline Spinal Neurons By Potentiated Ventricular Contractions And Other Mechanical Cardiac Stimuli," from *Journal of Physiology*, 1988, pp. 649-667.

Schwartz, et al., "Autonomic Mechanisms And Sudden Death—New Insights From Analysis Of Baroreceptor Reflexes In Conscious Dogs With and Without A Myocardial Infarction," from *Circulation*, vol. 78, No. 4, Oct. 1988, pp. 970-979.

Hobbs, et al., "Cardiac And Abdominal Vagal Afferent Inhibition Of Primate $T_9$—$S_1$ Spinothalamic Cells," from *The American Physiological Society*, 1989, pp. R889-R895.

Butler, et al., "Cardiac Responses To Electrical Stimulation Of Discrete Loci In Canine Atrial And Ventricular Ganglionated Plexi," from *The American Physiological Society*, 1990, pp. H1365-H1373.

Hull, et al., "Heart Rate Variability Before And After Myocardial Infarction In Conscious Dogs At High And Low Risk Of Sudden Death," from *The American College of Cardiology*, 1990, pp. 978-985.

Armour, M.D., "Intrinsic Cardiac Neurons," from *Journal of Cardiovascular Electrophysiology*, vol. 2, No. 4, Aug. 1991, pp. 331-341.

Chandler, et al., "Effects Of Vagal Afferent Stimulation On Cervical Spinothalamic Tract Neurons In Monkeys," from *Pain*, 1991, pp. 81-87.

Linderoth, M.D., et al., "Effects Of Sympathectomy On Skin And Muscle Microcirculation During Dorsal Column Stimulation: Animals Studies," from *Neurosurgery*, vol. 29, No. 6, 1991, pp. 874-879.

Vanoli, et al., "Vagal Stimulation And Prevention Of Sudden Death In Conscious Dogs With A Healed Myocardial Infarction," from *Circulation Research*, vol. 68, No. 5, May 1991, pp. 1471-1481.

Cardinal, et al., "Distinct Activation Patterns Of Idiovenricular Rhythms And Sympathetically-Induced Ventricular Tachycardias In Dogs With Atrioventricular Block," from *PACE*, Sep. 1992, pp. 1300-1306.

Fu, et al., "Vagal Afferent Fibers Excite Upper Cervical Neurons And Inhibit Activity Of Lumbar Spinal Cord Neurons In The Rat," from *Pain*, 1992, pp. 91-100.

Hobbs, et al., "Evidence That $C_1$ and $C_2$ Propriospinal Neurons Meditate The Inhibitory Effects Of Viscerosomatic Spinal Afferent Input On Primate Spinothalamic Tract Neurons," from *Journal of Neurophysiology*, vol. 67, No. 4, Apr. 1992, pp. 852-860.

Hobbs, et al., "Segmental Organization Of Visceral And Somatic Input Onto $C_3$—$T_6$ Spinothalamic Tract Cells Of The Monkey," from *Journal of Neurophysiology*, vol. 68, No. 5, Nov. 1992, pp. 1575-1588.

Chandler, et al., "A Mechanism Of Cardiac Pain Suppression By Spinal Cord Stimulation: Implications For Patients With Angina Pectoris," from *European Heart Journal*, 1993, pp. 96-105.

Huang, et al., "Effects Of Transient Coronary Artery Occlusion On Canine Intrinsic Cardiac Neuronal Activity," from *Integrative Physiological and Behavioral Science*, vol. 28, No. 1, Jan.-Mar. 1993, pp. 5-21.

Adamson, et al., "Unexpected Interaction Between β-Adrenergic Blockage And Heart Rate Variability Before And After Mycardial Infarction—A Longitudinal Study In Dogs At High And Low Risk For Sudden Death," from *American Heart Association, Inc.*, 1994, pp. 976-382.

Ardell, "Structure And Function Of Mammalian Intrinsic Cardiac Neurons," from *Neurocardiology*, 1994, pp. 95-114.

Armour, "Peripheral Autonomic Neuronal Interactions In Cardiac Regulation," from *Neurocardiology*, 1994, pp. 219-244.

Foreman, "Spinal Cord Neuronal Regulation Of The Cardiovascular System," from *Neurocardiology*, 1994, pp. 245-276.

Hull, et al., "Exercise Training Confers Anticipatory Protection From Sudden Death During Acute Myocardial Ischemia," from *Circulation*, 1994, pp. 548-552.

Linderoth, et al., "Sympathetic Mediation Of Peripheral Vasodilation Induced By Spinal Cord Stimulation: Animal Studies Of The Role Of Cholinergic And Adrenergic Receptor Subtypes," from *Neurosurgery*, vol. 35, No. 4, Oct. 1994, pp. 711-719.

Yuan, et al., "Gross And Microscopic Anatomy Of The Canine Intrinsic Cardiac Nervous System," from *The Anatomical Record*, 1994, pp. 75-87.

Armour, "Caine Intrinsic Cardiac Neurons Involved In Cardiac Regulation Possess $a_1$, $a_2$, $b_1$ and $b_2$ Adrenoreceptors," from *Can. J. Physiol. Pharmacol*, 1996, pp. 277-284.

Cardinal, et al., "Reduced Capacity Of Cardiac Efferent Sympathetic Neurons To Release Noradrenaline And Modify Cardiac Function In Tachycardia-Induced Canine Heart Failure," from *Can. J. Physiol. Pharmacol.*, 1996, pp. 1070-1078.

Chandler, et al., "Vagal, Sympathetic And Somatic Sensory Inputs To Upper Cervical ($C_1$-$C_3$) Spinothalamic Tract Neurons In Monkeys," from *The American Physiological Society*, 1996, pp. 2555-2567.

Zhang, et al., "Thoracic Visceral Inputs User Upper Cervical Segments To Inhibit Lumbar Spinal Neurons In Rats" from *Brain Research*, 1996, pp. 337-342.

Armour, et al., "Gross And Microscopic Anatomy Of The Human Intrinsic Cardiac Nervous System," from *The Anatomical Record*, 1997, pp. 289-298.

Croom, et al., "Cutaneous Vasodilation During Dorsal Column Stimulation Is Mediated By Dorsal Roots And CGRP," from *The American Physiological Society*, 1997, pp. H950-H957.

Hautvast, et al., "Spinal Cord Stimulation In Chronic Intractable Angina Pectoris: A Randomized Controlled Efficacy Study," from *American Heart Journal*, vol. 136, No. 6, 1998, pp. 1114-1120.

Schwartz, et al., "Autonomic Mechanisms And Sudden Death—New Insights From Analysis Of Baroreceptor Reflexes In Conscious Dogs With And Without Myocardial Infarction," from *Circulation*, vol. 78, No. 4, Oct. 1988, pp. 969-979.

Barron, et al., "Spinal Integration Of Antidromic Mediated Cutaneous Vasodilation During Dorsal Spinal Cord Stimulation In The Rat," from *Neuroscience Letter*, 1999, pp. 173-176.

Foreman, "Mechanisms Of Cardiac Pain," from *Annu. Rev. Physiol.*, 1999, pp. 143-167.

Linderoth, et al., "Physiology Of Spinal Cord Stimulation: Review And Update," from *Neuromodulation*, vol. 2, No. 3, 1999, pp. 150-164.

Qin, et al., "Chemical Activation Of Cervical Cell Bodies: Effects On Responses To Colorectal Distension In Lumbosacral Spinal Cord Of Rats," from *The American Physiological Society*, 1999, pp. 3423-3433.

Chandler, et al., "Intrapericardiac Injections Of Algogenic Chemicals Excite Primate $C_1$—$C_2$ Spinothalamic Tract Neurons," from *The American Physiological Society*, 2000, pp. R560-R568.

Foreman, et al., "Modulation Of Intrinsic Cardiac Neurons By Spinal Cord Stimulation: Implications For Its Therapeutic Use in Angina Pectoris," from *Cardiovascular Research*, 2000, pp. 367-375.

Hopkins, et al., "Pathology Of Intrinsic Cardiac Neurons From Ischemic Human Hearts," from *The Anatomical Record*, 2000, pp. 424-436.

Kember, et al., "Aperodic Stochastic Resonance In A Hysteretic Population Of Cardiac Neurons," from *The American Physical Society*, 2000, pp. 1816-1824.

Meyerson, et al., "Spinal Cord Stimulation," from *Bonica's Management of Pain*, 2001, pp. 1857-1876.

Ardell, "Neurohumoral Control Of Cardiac Function," from *Heart Physiology and Pathophysiology, Fourth Edition*, 2001, pp. 45-59.

Farrell, et al., "Angiotension II Modulates Catecholamine Release Into Interstitial Fluid Of Canine Myocardium In Vivo," from *Am J. Physiol. Heart Cir. Physiol.*, 2001, pp. H813-H822.

Kingma, Jr., et al., "Neuromodulation Therapy Does Not Influence Blood Flow Distribution Or Left-Ventricular Dynamics During Acute Myocardial Ischemia," from *Autonomic Neuroscience: Basic & Clinical*, 2001, pp. 47-54.

Tanaka, et al., "Low Intensity Spinal Cord Stimulation May Induce Cutaneous Vasodilation Via CGRP Release," from *Brain Research*, 2001, pp. 183-187.

Qin, et al., "Responses And Afferent Pathways Of Superficial And Deeper $C_1$—$C_2$ Spinal Cells To Intrapericardial Algogenic Chemicals In Rats," from *The American Physiological Society*, Dec. 2000, pp. 1522-1532.

Armour, et al., "Long-Term Modulation Of The Intrinsic Cardiac Nervous System By Spinal Cord Neurons In Normal And Ischaemic Hearts," from *Autonomic Neuroscience: Basic & Clinical*, 2002, pp. 71-79.

Chandler, et al., "Spinal Inhibitory Effects Of Cardiopulmonary Afferent Inputs In Monkey: Neuronal Processing In High Cervical Segments," from *J. Neurophysical*, 2002, pp. 1290-1302.

Cardinal, et al., "Spinal Cord Activation Differentially Modulates Ischaemic Electrical Responses To Different Stressors In Canine Ventricles," from *Autonomic Neuroscience: Basic & Clinical*, 2004, pp. 37-47.

Ardell, "Intrathoracic Neuronal Regulation Of Cardiac Function," from *Basic and Clinical Neurocardiology*, 2004, pp. 118-152.

* cited by examiner

CLOSED-LOOP NEUROMODULATION FOR PREVENTION AND TREATMENT OF CARDIAC CONDITIONS

RELATED CASES

This case claims priority to the following provisionally-filed cases:

U.S. Provisional Patent Application Ser. No. 60/294,072, filed May. 29, 2001, entitled "Closed-Loop Neuromodulation for Prevention and Treatment of Cardiac Conditions";

U.S. Provisional Patent Application Ser. No. 60/243,393, filed Oct. 26, 2000, entitled "Method and Apparatus to Minimize the Effects of a Cardiac Insult";

U.S. Provisional Patent Application Ser. No. 60/243,536, filed Oct. 26, 2000, entitled "Method and Apparatus to Minimize the Effects of a Cardiac Insult"; and U.S. Provisional Patent Application Ser. No. 60/243,609, filed Oct. 26, 2000, entitled "Method and Apparatus for Electrically Simulating the Nervous System to Improve Ventricular Dysfunction, Heart Failure, and Other Cardiac Conditions", all of which are incorporated herein by reference in their entireties.

This case is related to, and contains subject matter in common with, the following applications:

U.S. patent application Ser. No. 09/999,723 filed on Oct. 26, 2001 entitled "Method and Apparatus to Minimize the Effects of a Cardiac Insult";

U.S. patent application Ser. No. 09/999,722 filed on Oct. 26, 2001 entitled "Method and Apparatus to Minimize the Effects of a Cardiac Insult"; and U.S. patent application Ser. No. 10/039,307 filed on Oct. 26, 2001 entitled "Method and Apparatus for Electrically Stimulating The Nervous System to Improve Ventricular Dysfunction, Heart Failure, and Other Cardiac Conditions".

FIELD OF THE INVENTION

This invention relates generally to a method and apparatus for electrically stimulating certain nerves to alter conditions within the heart, and, more particularly, to employing a closed-loop system to control nerve stimulation to treat various cardiac conditions.

DESCRIPTION OF THE RELATED ART

Various cardiac conditions, such as supraventricular arrhythmias, angina pectoris, and ventricular dysfunction or heart failure, have been treated by electrical stimulation of the spinal cord, vagus and other nerves. Typically, electrodes are implanted in the patient adjacent the spinal area and electrically excited to produce desirable effects on the functioning of the heart. For example, a paper entitled "Vagal Tuning" by Bilgutay et. al., published in the Journal of Thoracic and Cardiovascular Surgery, Vol. 56, No. 1, July 1968, pp. 71–82, discusses a system that delivers electrical stimulation to the vagus nerve using silastic coated, bipolar electrodes, such as those described in U.S. Pat. No. 3,421, 511. The electrodes are surgically implanted around the intact nerve or nerves and a controlled current is delivered thereto. The electrodes pass the current to the nerve(s), producing a decreased heart rate while still preserving sinus rhythm in the patient. Low amplitude stimulation has also been employed to control induced tachycardias and ectopic beats.

Angina pectoris and paroxysmal atrio-ventricular junctional or supraventricular tachycardias have also been treated by stimulating the carotid sinus nerve via implanted electrodes. For example, a paper entitled "Carotid Sinus Nerve Stimulation in the Treatment of Angina Pectoris and Supraventricular Tachycardia," published in California Medicine, 112:41–50, March 1970, describes a system in which patients may electrically stimulate their carotid sinus nerve when they sense angina and/or supraventricular stachycardia.

Delivery of electrical stimulation to the nervous system using an implanted electrode has been found particularly effective in the relief of chest pain, such as angina pectoris, that often accompanies myocardial ischemia. For example, U.S. Pat. No. 5,058,584 to Bourgeois, incorporated herein by reference in its entirety, discloses a system and method for treating such chest pain using electrical stimulation within the epidural space of the spinal cord. This treatment is provided only after a symptomatic level of activity is reached as sensed by an accelerometer or other activity sensor. Similarly, U.S. Pat. No. 6,058,331 to King, also incorporated herein by reference in its entirety, discusses a system and method for treating ischemia by automatically adjusting electrical stimulation to the spinal cord, peripheral nerve, or neural tissue ganglia based on a sensed patient condition. U.S. Pat. No. 5,199,428 to Obel et al., incorporated herein by reference in its entirety, discloses a system for stimulating the epidural space with continuous and/or phasic electrical pulses using an implanted pulse generator upon the detection of myocardial ischemia to decrease cardiac workload, and thereby reduce cell death related to the ischemic event. U.S. Pat. No. 5,824,021 to Rise, incorporated herein by reference in its entirety, discusses a system and method for providing spinal cord stimulation to relieve angina, and to further provide a patient notification that an ischemic event is occurring. This spinal cord stimulation is provided only after the ischemia is already detected.

In addition to the above-described systems, other systems have been disclosed to provide nerve stimulation following the onset of predetermined condition. U.S. Pat. No. 6,134, 470 to Hartlaub describes a system for utilizing spinal cord stimulation to terminate tachyarrhythmias. The stimulation is provided only after the tachyarrhythmias, or a precursor thereto, has been detected. U.S. Pat. No. 3,650,277 discloses a system for stimulating the left and right carotid sinus nerves in response to the detection of elevated mean arterial blood pressure to alleviate hypertension.

The systems discussed above deliver stimulation upon the onset of a predetermined physical condition such as ischemia or tachyarrhythmia. These systems do not provide treatments to anticipate the on-set of a particular physiological condition so that the condition may be prevented. Furthermore, such systems do not provide a preventative system that utilizes a closed-loop mechanism to monitor one or more physiologic conditions to modulate therapy. Finally, prior art systems utilize implanted electrodes to perform spinal cord stimulation in response to an already-occurring physiological condition. Such systems do not address the need for more acute therapies such as transcutaneous electrical stimulation (TENs) or subcutaneous stimulation that may be administered on an as-needed basis. What is needed, therefore, is an improved system that addresses the foregoing limitations.

SUMMARY OF THE INVENTION

The current invention involves a neuromodulation system to provide stimulation to at least a portion of the nervous system of the body. The stimulation is provided using one or more subcutaneous, cutaneous, or implanted electrodes. The stimulation is provided in anticipation of a cardiac insult, wherein "cardiac insult" in this context is intended to include, but is not limited to, mechanical, chemical, or electrical impairment or damage of cardiac tissue due to conditions such as heart failure, ventricular tachycardia, supraventricular tachycardia, ischemia, imbalance of autonomic tone, or the like.

In one embodiment, the current invention provides a system and method to provide stimulation at locations adjacent the spinal region and on the chest wall. Such stimulation has been shown to improve cardiac function, to limit ischemic attacks, to reduce sympathetic activity of the cardiac tissue, and to reduce the likelihood and/or the severity of ventricular arrhythmia. Thus, the electrical stimulation produces effects similar to those induced by prescription beta-blocker drugs. This type of stimulation has been shown to reduce cardiac work, improve heart function, vasodilate peripheral arterioles and increase blood flow to the limbs.

According to the invention, one or more electrodes may be placed adjacent one or more of the T1–T12 vertebrae, with the T1–T4 locations being preferred. Alternatively, the electrodes may be placed adjacent the chest wall or anywhere within a region of the T1–T5 dermatomes. The position of the electrodes may be, for example, in the pectoral region of the left chest located near the pectoral muscle with stimulation of the musculocutaneous and thoracic nerves. In another example, the electrodes may be positioned in the axillary region beneath the left arm with stimulation provided to the musculocutaneous, brachialcutaneous and thoracodorsal nerves. In yet another embodiment, one or more electrodes are proximate to the external housing of an implanted device to stimulate nerves adjacent to the device.

The inventive system and method may be operated in a closed-loop mode. In this mode, one or more physiological parameters may be sensed using physiological sensors. The sensed physiological signals may be used to predict the onset of an insult. These signals may also be used to modulate delivery of the stimulation parameters such as pulse width, amplitude, frequency, and the like. Moreover, these signals may be used to determine the length of time to continue stimulation.

According to yet another embodiment, the inventive system stores data signals indicative of past electrical stimulation so that future stimulation may be optimized. This stored data may also be used by healthcare professionals for treatment and diagnosis.

In yet another aspect of the instant invention, a method is provided for protecting cardiac tissue from insult. The method comprises delivering electrical stimulation to one or more predetermined portions of the nervous system in a patient's body in anticipation of a cardiac insult, and monitoring one or more physiologic indices of the body to determine whether the delivered therapy is effective.

In another aspect of the instant invention, a system is provided for protecting cardiac tissue from insult. The apparatus is comprised of a sensing circuit, stimulation circuit, and a control circuit. The sensing circuit senses at least one physiologic parameter. The stimulation circuit provides the electrical stimulation to the one or more nerves. The control circuit is coupled to the sensing circuit and to the stimulation circuit to control the stimulation circuit based on the at least one physiologic parameter sensed by the sensing circuit.

Figure 1A:
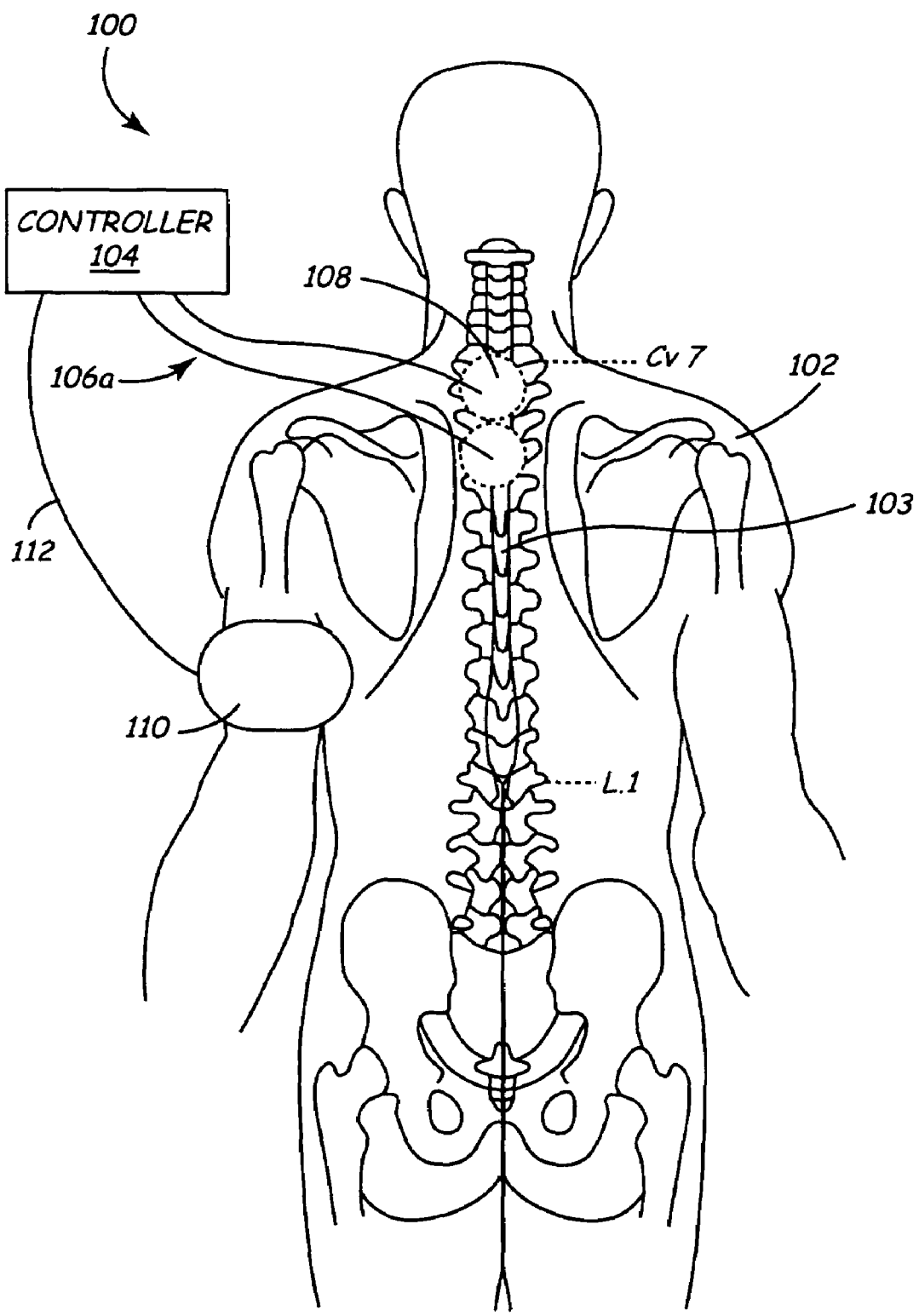
FIG. 1A illustrates a stylized representation of a posterior view of a patient with electrodes positioned thereon.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but, on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Illustrative embodiments of a method and apparatus for providing improved cardiac function according to the present invention are shown in the Figures. As will be readily apparent to those skilled in the art upon a complete reading of the present application, the present method and apparatus are applicable to a variety of systems other than the embodiment illustrated herein.

In the illustrated embodiments, a method and apparatus for performing spinal cord, vagus nerve, peripheral nerve, transcutaneous, and/or subcutaneous electrical stimulation to proactively modulate autonomic effects on the cardiovascular system is provided. Use of the stimulation minimizes arrhythmia, heart failure, and damage to cardiac myocytes due to the occurrence of a predicted and subsequent ischemic event. Such stimulation may be provided to one or more portions of the nervous system to also promote electrical stability of the heart and to prevent or reduce the chance for a subsequent episode involving fibrillation. As described in greater detail below, the current method and apparatus may employ a closed-loop control mechanism to initiate and regulate this stimulation.

Generally, the instant invention is directed to a method and apparatus for improving the efficiency of operation of the heart and may be used to reduce the likelihood of imminent cardiac insults. Therapeutic benefits associated with the instant invention may be derived from application of the instant invention to a wide variety of cardiac conditions. Thus, as used in the instant application, the phrase "cardiac insult" is intended to include, but is not limited to, damage or mechanical, chemical, or electrical impairment of cardiac tissue due to conditions such as heart failure, ventricular tachycardia, supraventricular tachycardia, ischemia, imbalance of autonomic tone, or the like. In the illustrated embodiment, the current invention may also be utilized to treat ventricular dysfunction or heart failure.

Figure 1B:
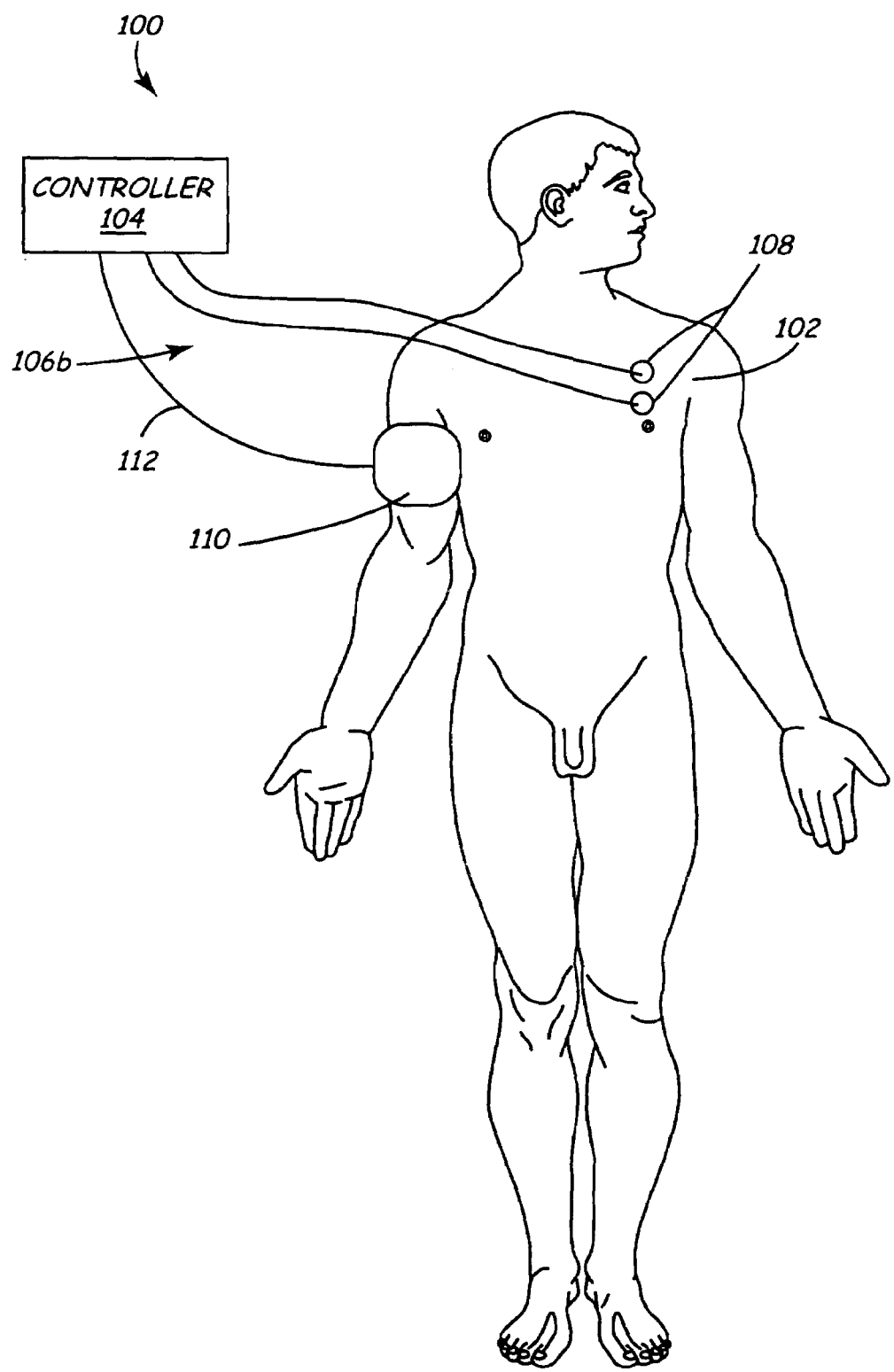
FIG. 1B illustrates a stylized representation of an anterior view of a patient with electrodes positioned thereon.

As shown in FIGS. 1A and 1B, an external system 100 provides stimulation to a patient 102 at locations adjacent the spinal region and on the chest wall using leads 106*a* and 106*b*, respectively. Such spinal cord stimulation (SCS) has been shown to improve contractibility, to further improve the pressure-volume relationship within the heart, and to reduce sympathetic activity of the cardiac tissue to reduce the likelihood of ventricular arrhythmias. Thus, the electrical stimulation produces effects similar to those induced by prescription beta-blocker drugs. This type of stimulation has been shown to vasodilate peripheral arterioles and increase blood flow to the limbs. The stimulation may further cause the production of neuropeptides such as CGRP, NO, and VIP that are known vasodilators, which may assist in redirection of blood flow from regions of high flow to regions of low flow. This further improves the efficiency of the heart. In ischemic dilated cardiomyopathy patients, this therapy may suppress or reduce subendocardial ischemia, and hence be cardio-protective. Electrical stimulation may further result in improvements in operational efficiency and function of cardiac tissue even in the presence of reduced blood supply.

When an SCS lead 106*a* is utilized, the lead configuration may be of the type described in U.S. Pat. No. 4,549,556 issued to Tarjan et al. or in commonly assigned U.S. Pat. No. 5,255,691 issued to Otten, U.S. Pat. No. 4,044,774 issued to Corbin et al. or U.S. Pat. No. 5,360,441 issued to Otten, all incorporated herein by reference in their entireties. Alternatively, the electrode may correspond to commercially-available spinal cord stimulation leads such as the Medtronic Model 3487A or 3888 leads which include a plurality, e.g. four spaced apart distal electrodes that are adapted to be placed adjacent the spinal cord 103, for example in the intrathecal space, in the epidural space, or adjacent the roots of nerves branching off of the spinal cord. The proximal end of the SCS lead 116*a* may carry a quadripolar in-line connector assembly inserted into a connector block of controller 104. Two or more of the electrodes may be employed to stimulate the spinal column. Leads with fewer or more than four electrodes may of course also be employed.

In another embodiment, the electrodes 108 may be applied cutaneously or subcutaneously adjacent any of the T1–T12 vertebrae or in any of the C1–C8 locations, and most preferably, any of the T1–T4 vertebrae (see FIG. 1A), or may be placed adjacent the chest wall (see FIG. 1B). The electrodes 108 may take on any of a variety of forms of cutaneous or subcutaneous electrodes. For example, conventional surface mounted electrodes, such as are commonly used in conjunction with Transcuteous Neurological Stimulator (TENS) units, may be employed. These surface mounted electrodes may be fixed to the patient 102 via any of a variety of conventional mechanical or chemical mechanisms or may be simply held in place by friction, adhesives, and gravity or other mechanisms. In some embodiments, the electrodes 108 may be disposed immediately adjacent nerve bundles associated with any of the T1–T12 vertebrae.

Conventional subcutaneous electrodes may be surgically inserted into the patient's body. In fact, subcutaneous stimulation may be provided using leads of the type that are commonly used for pacing the heart. The implantable electrodes may be placed subcutaneously to stimulate underlying muscles, overlying cutaneous nerves, passing somatic nerves, or a combination thereof. For example, various commercially available leads, such as the Pisces®, Pisces Quad Plus®, and Octad® model leads, commercially-available from Medtronic Corporation, are examples of leads that may be used for this purpose. This subcutaneous or cutaneous placement may be desirable in emergency situations such as en route to a medical care facility following symptoms indicative of an impending cardiac insult.

As discussed above, subcutaneous electrodes may be carried on leads and inserted near nerve tissue using a delivery device such as a needle. In other instances, subcutaneous electrodes may be carried on the surface of an implanted medical device such as disclosed in commonly-assigned U.S. Pat. No. 5,292,336 incorporated herein by reference in its entirety. Alternatively, such electrodes may be electrically-isolated from the can, as disclosed in commonly-assigned U.S. Pat. No. 5,331,966 incorporated herein by reference in its entirety.

In one embodiment, a paddle-type (flat) lead having a surface area between one square cm and five square inches or more may be used to accomplish the subcutaneous stimulation. Such a lead may be formed of an insulative material, with programmable electrodes on one or more of the flat sides of the lead for either skin stimulation, muscle stimulation, or both. According to this embodiment, the paddle-type lead may be between four and ten millimeters wide so as to be readily passable through a needle such as a twelve-gage needle before it unfolds. In one embodiment, the special delivery needle includes an oval or rectangular cross-section of appropriate size to allow for passage of the lead. Electrodes may be provided on one or both sides of the paddle lead.

In another embodiment, electrodes may be provided on both sides of the lead, with the electrodes employed for stimulation at a given time being selectively enabled by a user. Alternatively, the system may be programmable to select the type of tissue to be stimulated. This is desirable since in some instances, it may be beneficial to provide stimulation to only spinal neurons, whereas in other instances it may be desirable to also stimulate skin, muscle, or any combination of the nervous tissues. Various electrode combinations could be provided to allow for selective enabling of the stimulation in this manner.

As noted above, many types of electrode systems may be adapted for use with the current invention, including cutaneous, subcutaneous, and implanted electrodes. These electrodes are coupled to controller 104 so that electrical signals supplied by the controller 104 provide electrical stimulation to nervous tissue in the skin, muscle, or spinal canal of the patient. The controller 104 may take the form of an external device as shown in FIGS. 1A and 1B. This is useful in providing therapeutic signals to a patient who is anticipating exertion or any other type of event that may cause ischemia.

Figure 1C:
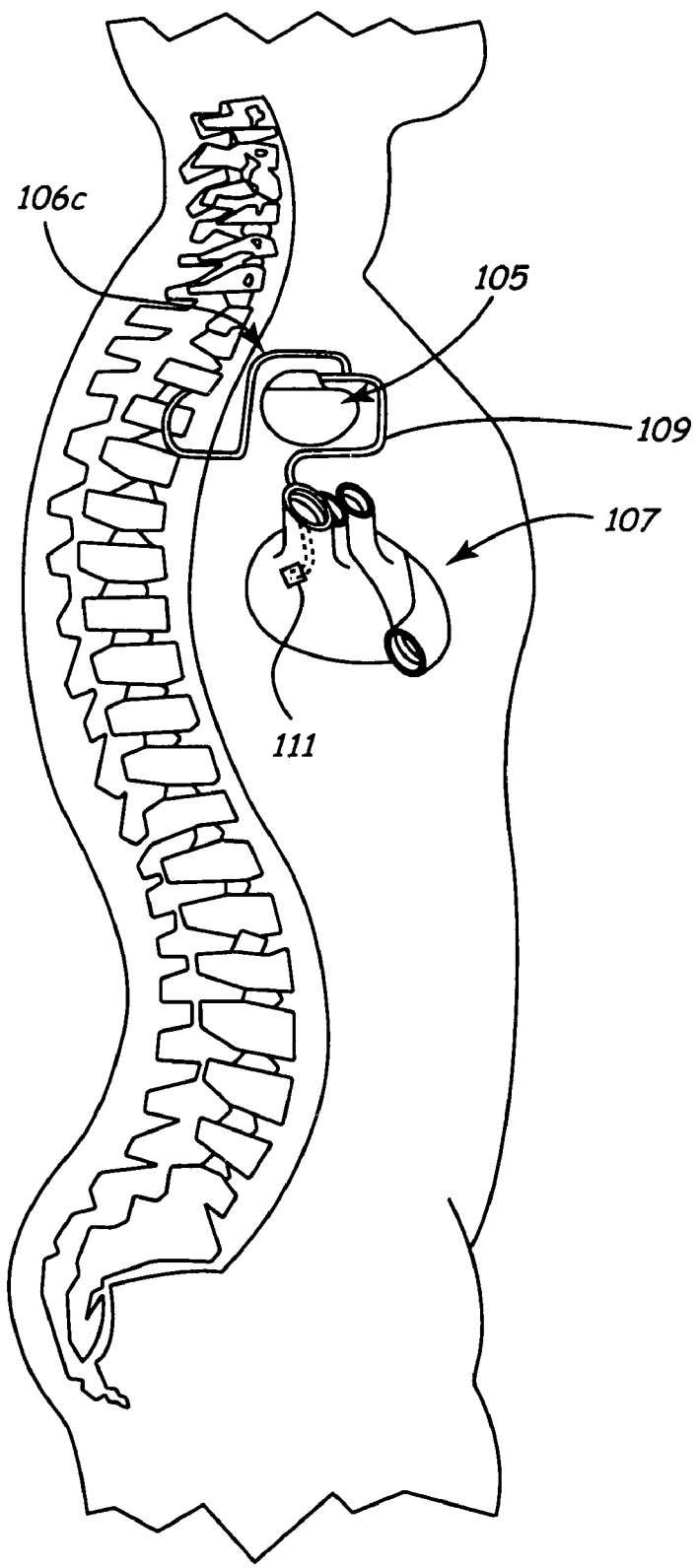
FIG. 1C is a diagram illustrating an implantable stimulation device implanted within a patient.

In those situations in which a patient has a history of cardiac events, it is generally useful to construct the controller 104 in a housing 105 designed to be implantable within the human body, as shown in FIG. 1C. In this embodiment, implanted lead 106c is employed to deliver SCS according to the invention. This housing may optionally include a pacing andlor cardioverter/defibrillator stimulation circuit for generating cardiac stimulation signals to the heart 107 using one or more leads 109, as is known in the art. Leads 109 may carry one or more physiological sensors 111 for sensing physiological signals, as is discussed below. Additionally, or in the alternative, the housing may also include a drug delivery device such as a drug pump coupled to a drug delivery catheter that may be used with the nerve stimulation to prevent anticipated physiological insults.

In one embodiment, controller 104 may be programmed for either automatic or manual operation. That is, controller 104 may utilize one or more conventional sensors such as sensor 111 to sense signals that predict the possible on-set of physiologic conditions such as ventricular dysfunction, ischemia, heart failure, or any other type of cardiac insult. These sensors may be any of the types known in the art for sensing physiological signals, including pressure, oxygen, activity, temperature, and blood flow sensors. Exemplary sensors are disclosed in U.S. Pat. No. 4,903,701 issued to Moore et al., U.S. Pat. No. 5,564,434, issued to Flalperin et al, U.S. Pat No. 4,428,378, issued to Anderson et al., U.S. Pat. No. 5,464,434, issued to Alt or U.S. Pat. No. 5,330,505, issued to Cohen, all incorporated herein by reference in their entireties.

Upon anticipation of the cardiac event, the controller 104 may automatically begin therapeutic treatment of the patient by electrically stimulating the selected nervous tissue(s). Alternatively, a patient or authorized person may manually activate the controller 104 to begin this therapeutic treatment. Manual activation may be accomplished by any of a variety of mechanisms. For example, where the controller 104 is implanted in the patient, activation may be accomplished by wireless communication or the like.

In addition to the preventative treatment discussed above wherein therapy is provided prior to the onset of a predetermined condition, treatment may continue during an event should the initial therapy fail. For example, acute subcutaneous or cutaneous stimulation may be used while a heart attack is in progress during transport to a medical facility or in an emergency room prior to patient stabilization. Such stimulation could be continued until a cardiovascular intervention procedure is initiated, or even continued for several weeks past the incident.

Figure 2:
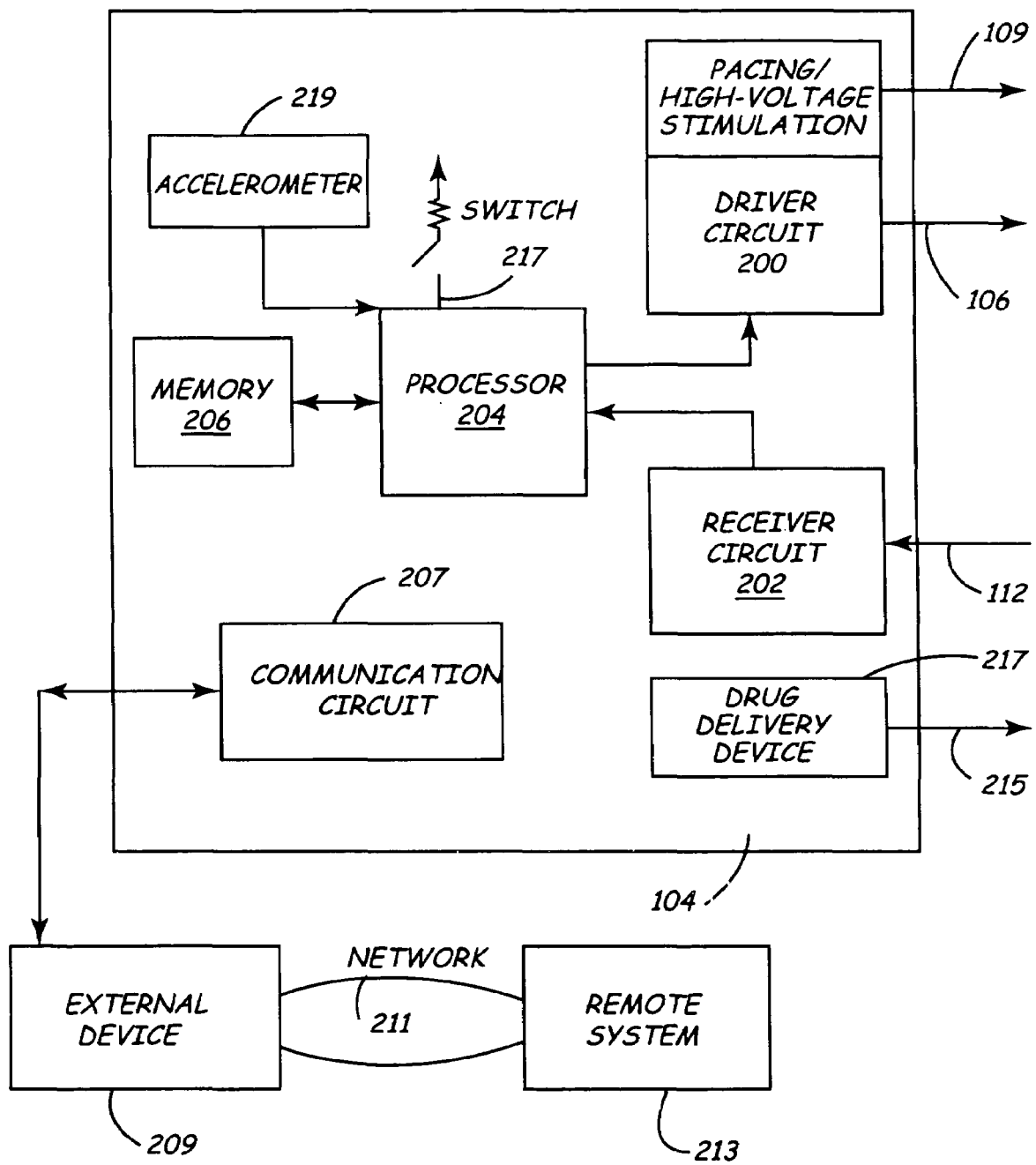
FIG. 2 illustrates a stylized block diagram of a controller of FIG. 1.

FIG. 2 illustrates a block diagram of one embodiment of the controller 104. Generally, the controller 104 is comprised of one or more driver circuits 200 and receiver circuits 202. The driver circuits 200 are generally responsible for providing the stimulating signals over the lines 106 to the electrodes 108. That is, a processor 204, operating under software or hardware control, may instruct the driver circuit 200 to produce a stimulating signal having a set of preselected, desired parameters, such as frequency, duty cycle, duration, waveform shape, amplitude, voltage and magnitude. As noted above, driver circuits 200 may optionally include circuits 201 to generate pacing and/or high-voltage stimulation to the heart on leads 109.

The receiver circuits 202 are generally responsible for receiving signals over the lines 112 from the sensors 110 and 111, and processing those signals into a form, such as a digital format, which may be analyzed by the processor 204 and/or stored in a memory 206, such as a dynamic random access memory (DRAM). The memory 206 may also store software, which is used to control the operation of the processor 204.

In one embodiment, signals stored in memory 206 may be transferred via a communication circuit 207 such as a telemetry circuit to an external device 209 such as a programmer. These signals may be stored in the external device, or transferred via a network 211 to a remote system 213 which may be a repository or some other remote database. Network 211 may be an intranet, internet system such as the world-wide web, or any other type of communication link.

Controller 104 may further include a reed switch 217. This type of switch mechanism may be closed using a magnet in the embodiment wherein the controller is implanted. Controller may further include an accelerometer 219, as will be discussed further below.

As noted above, controller 104 may further include a drug delivery device 213 that may comprise a pump coupled to a catheter 215. Exemplary implantable drug delivery systems that may be adapted to deliver biologically-active agents in conjunction with SCS or other nerve stimulation are disclosed in U.S. Pat. No. 5,607,418, issued to Arzbaecher, U.S. Pat. No. 5,220,917, issued to Cammilli, U.S. Pat. No. 4,146,029, issued to Ellinwood and U.S. Pat. No. 5,330,505, issued to Cohen, all incorporated herein by reference in their entireties.

As noted above, in one embodiment, delivery of the stimulation via driver circuit 200 may be modified based on a variety of measurable physiologic parameters used in a closed loop control system. As depicted in FIGS. 1A, 1B, and 1C representative sensor 110 or 111 may be positioned adjacent or within the body of the patient 102 to sense various physiological conditions, which are communicated back to the controller 104 The measured physiological conditions may be used as an indication of the patient's response to the therapy being administered by the controller 104 That is, a positive physiological response may be used as an indication that the therapy is achieving the desired result. The sensed physiological conditions may be used to adjust the parameters of the stimulation. For example, the controller 104 may measure and record cardiac pulse pressure. A change in the cardiac pulse pressure over time may be used in a closed-loop system to adjust delivery of stimulation. For example, if the controller 104 detects that the cardiac pulse pressure has declined over time, then the parameters of the stimulation may be adjusted in an attempt to increase the cardiac pulse pressure. On the other hand, where the controller 104 observes a consistent, appropriate cardiac pulse pressure, then the stimulation may be continued, as a desired result is being achieved by the stimulation. On the other hand, where the controller 104 observes continued high, or even rising, cardiac pulse pressure, then the parameters of the stimulation may be adjusted in an attempt to lower the cardiac pulse pressure over time.

Figure 3:
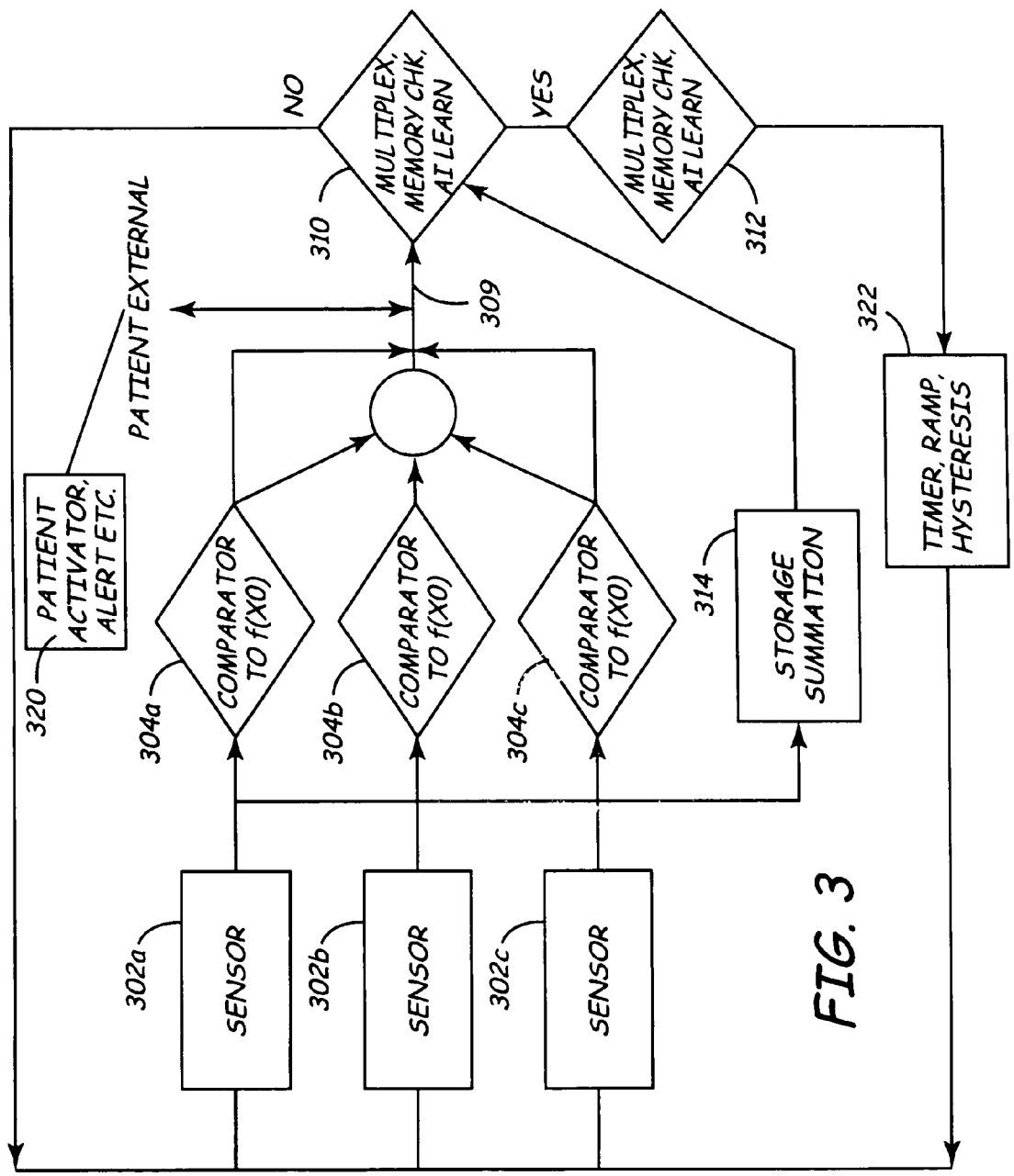
FIG. 3 illustrates a stylized control diagram of a control routine that may be performed by the controller of FIGS. 1 and 2.
Figure 4:
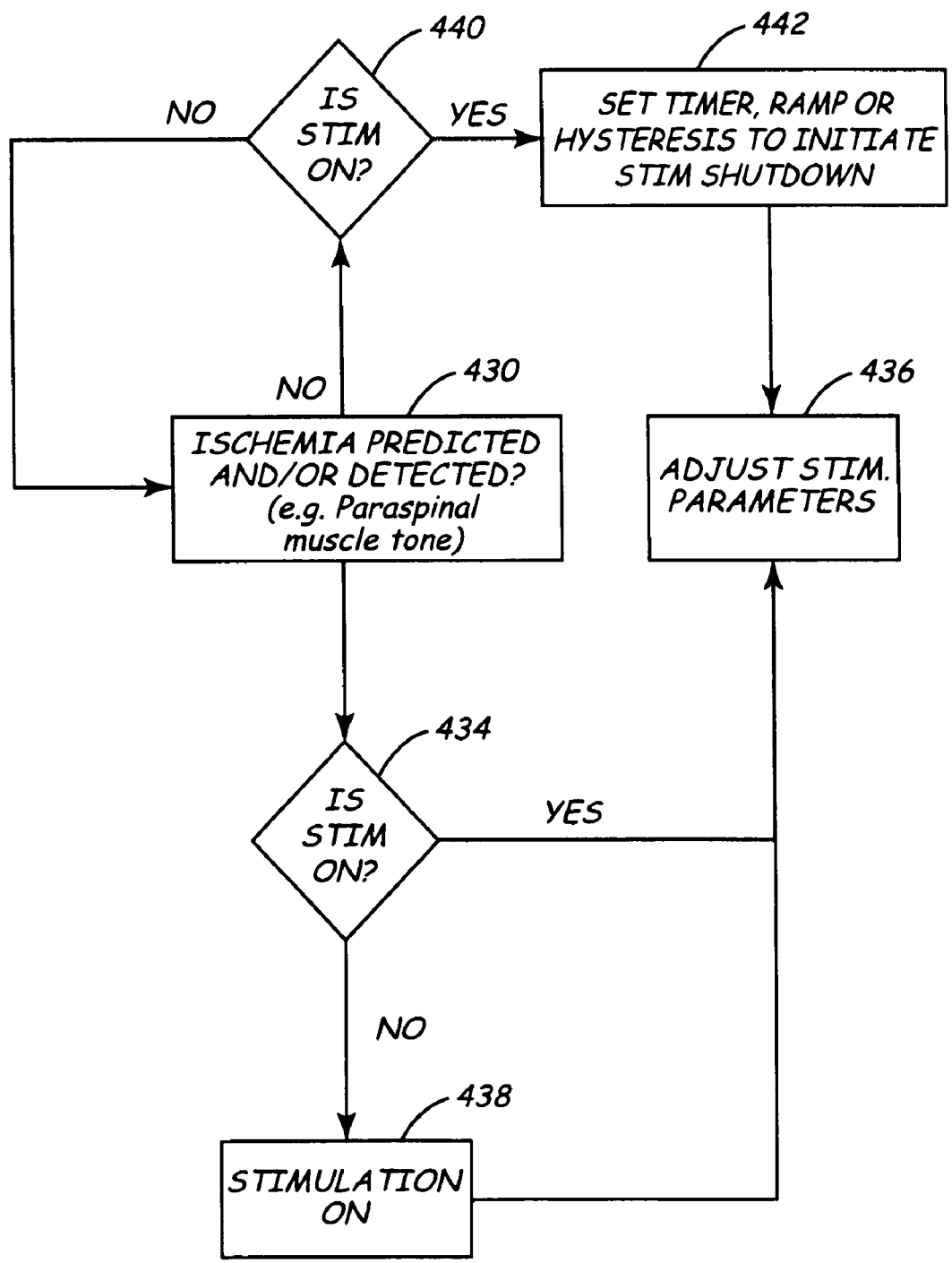
FIG. 4 illustrates a stylized flowchart of an exemplary control routine that may be performed by the controller of FIGS. 1 and 2.

The overall general operation of the controller 104 may be appreciated by reference to a control diagram and flowchart depicted in FIGS. 3 and 4. Those skilled in the art will appreciate that the control diagram and flowchart illustrated herein may be used to represent either software that may be executed by the processor 204 or hardware configured to operate to perform the functions set forth in the flowchart. Thus, either hardware or software may be employed without departing from the spirit and scope of the instant invention.

FIG. 3 depicts a generalized mode of closed loop operation. Through a sensor or combination of sensors, the system evaluates a physiologic state. This includes predicting (and later, detecting the continuation of) ischemia, an increased risk of VT/VF, a cardiovascular decompensation, and/or other types of cardiac insults to be discussed below. Any of the sensing systems listed below may be used to monitor physiological parameters to accomplish this function.

In response to the detection of a particular physiologic state, the system adjusts the stimulation parameters to treat the detected or predicted abnormality. The system may also record trends in the sensed data and the effects or impact of a prior stimulation intervention. In one embodiment, the system may include an artificial intelligence system that allows the device to learn from the effectiveness of the prior therapy. The system thereby becomes customized to deliver therapy that is optimally tailored for the individual patient.

After stimulation is initiated in response to an anticipated or detected insult, stimulation parameters may be adjusted. Such parameters may include stimulation pulse width, amplitude, frequency, duty cycle, and waveform shape. These parameters may be continually modified as the response is monitored so that the optimal treatment may be delivered. After the insult such as an ischemic episode has subsided, stimulation may be discontinued after an appropriate delay. A ramp-down process may be provided to allow for some hysteresis. Sensed data and device parameters may be transferred to an external device such as a programmer using a communication system such as a telemetry circuit. The physician may then evaluate the data and determine whether the delivered therapy requires modification, and whether it is desirable to enable the device to provide patient-initiated therapy in a manner to be discussed below. Additionally, the data may provide valuable information that may be used to deliver more effective manual therapy.

In FIG. 3, one or more sensors shown as sensors 302a through 302c are used to measure physiologic conditions. The measured signals may be compared against a threshold value by one or more comparators 304a through 304c. The results of the comparisons may be summed, or otherwise processed, with the processed data set being provided on line 309. If this result indicates that electrical stimulation is required, as determined by block 310, therapy is initiated. Therapy is initiated and controlled by a processing circuit, as represented by block 312. This processing circuit 312 provides the closed-loop feedback control used to modulate the level of therapy delivered. When therapy is to be discontinued, a ramp-down circuit shown in block 322 may be used to gradually discontinue the stimulation.

In one embodiment, artificial intelligence capability may be provided by the logic of block 310. This artificial intelligence analyzes the effectiveness of previously delivered therapy to adjust current therapy delivery techniques. Therapy is thereby tailored to individual patient needs.

According to another manner of initiating therapy, the signals provided by the sensors 302a through 302c may be combined to generate a cumulative signal indicative of a patient's overall physiologic condition. This may be accomplished using a summation circuit 314, for example. The cumulative signal may be provided along with, or in place of, the signal on the line 309 for use in determining whether therapy should be initiated or modulated. In addition to closed-loop operation, FIG. 3 also includes open-loop methods of initiating therapy, including patient-initiated therapy shown in block 320.

FIG. 4 illustrates a flowchart representation of one embodiment of operating a closed-loop system according to the current invention. In block 430 of FIG. 4, a determination is made as to whether ischemia is anticipated. This determination is based on monitored physiological parameters that may include detection of physical activity, a change in the ST segment, change in paraspinal muscle tone, and/or a change in heart rate. Other parameters may be monitored in a manner to be discussed further below.

According to one aspect of the invention, electrical stimulation is provided when the tone in the paraspinal muscles is increasing, since this is an indicator of anticipated visceral complications. Detection of this increase in muscle tone could be accomplished using an externally-positioned strain gage, for example. Thus, electrical stimulation may be applied prior to the onset of actual ischemic so that cardiac tissue maybe protected in an anticipatory manner. Electrical stimulation may also continue while the muscle tone remains at a predetermined rigidity. In one embodiment, a rate-responsive sensor such as an accelerometer or other appropriate sensor may be used to sense the level of activity, and adjust the stimulation levels according to the activity level.

If ischemia is anticipated, and the stimulation has already been initiated as detected by block 434, the stimulation level may be adjusted in block 436 based on the monitored parameters. This may include adjusting the rate, amplitude, duration, or waveform shape of electrical stimulation pulses applied to the electrodes 108. If stimulation has not yet been initiated, it may be activated in block 438. If artificial intelligence is provided, the level and/or type of stimulation may be correlated with the physiologic result of the stimulation so that therapy may be adjusted in the future. The stimulation may be modulated in block 436, with the monitoring of patient condition continuing in block 430. Stimulation may continue after the ischemia is actually detected.

If ischemia is not anticipated and/or detected in block 430, and stimulation is activated, as indicated by block 440, stimulation may be discontinued, as shown in block 442. In one embodiment this may be accomplished using a timer and a ramp-down mechanism to gradually disable the stimulation therapy.

Figure 5:
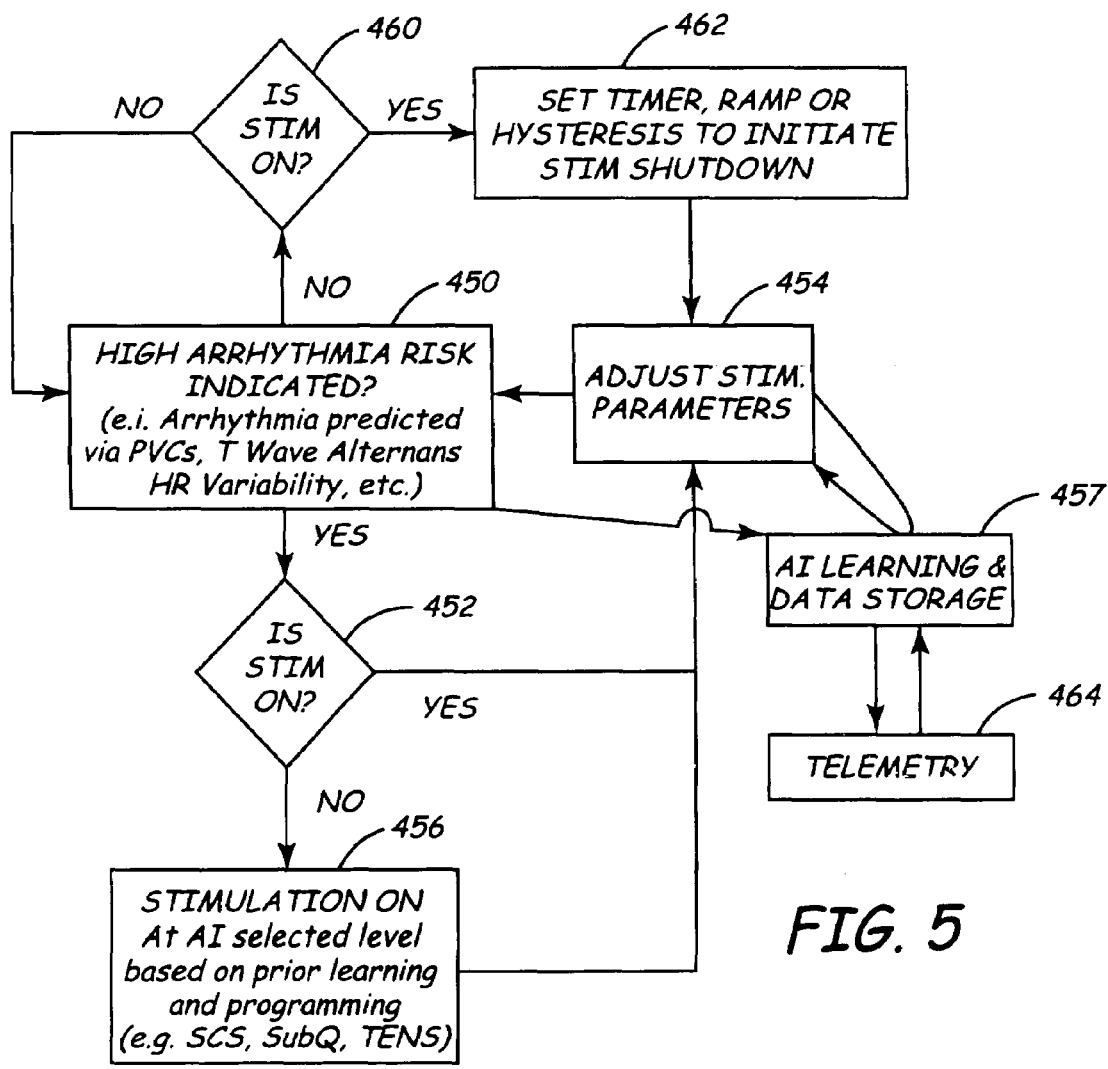
FIG. 5 illustrates a stylized flowchart of an alternative control routine that may be performed by the controller of FIGS. 1 and 2.

FIG. 5 illustrates a flowchart representation of another embodiment of operating a closed-loop system to predict arrhythmias according to the current invention. In block 450, a determination is made as to whether a high-risk of arrhythmia is indicated. This may be indicated by premature ventricular contractions (PVCs), T-wave alternans, heart rate variability, and QT prolongation, for example. If a high risk of arrhythmia does exist, and the stimulation has already been initiated as detected by block 452, the stimulation level may be adjusted in block 454 based on the monitored parameters. This may include adjusting the rate, amplitude, duration, or waveform shape of electrical stimulation pulses applied to the electrodes 108. If stimulation has not yet been initiated, it may be activated in block 456. If artificial intelligence is provided as shown in block 457, the level and/or type of stimulation may be correlated with the physiologic result of the stimulation so that therapy may be adjusted in the future based on "learned" patient responses.

The stimulation may be modulated in block 454, with the monitoring of patient condition continuing in block 450. Stimulation may continue after the arrhythmia is actually detected.

If arrhythmia is not anticipated and/or detected in block 450, and stimulation is activated, as indicated by block 460, stimulation may be discontinued, as shown in block 462. As discussed above, this may be accomplished using a timer and a ramp-down mechanism to gradually disable the stimulation therapy.

In one embodiment, data may be provided to an operation (clinician) so that the clinician may adjust the level and/or type of stimulation. This transfer of data may be accomplished using a telemetry mechanism, as shown in block 464. This allows the operator to optimize stimulation, control the degree or type of system "learning", and otherwise interact with the system to optimize performance.

As noted above, a closed-loop system may be utilized to control initiation and delivery of the electrical stimulation. The closed-loop system may utilize one or more physiological sensors known in the art to sense one or more physiological conditions that will be utilized to control therapy. Such sensors may include activity sensors, sensors for detecting cardiac electrical or mechanical activity, mechanisms for detecting autonomic activity or hemodynamic parameters, sensors for measuring blood chemistry, and mechanisms for tracking time-of-day. A partial exemplary listing of select types of sensing mechanisms that may be utilized in the closed-loop system for predicting cardiac insults are summarized in Table 1 below. The following table summarizes the types of sensors that may be employed to predict and/or detect a corresponding physiologic condition. Any one or more of the sensing devices and/or other sensing mechanisms known now or in the future for sensing physiological parameters may be employed without departing from the spirit and scope of the current invention.

In Table I, column 1 lists general categories of sensors, column 2 corresponds to a particular physiologic parameter that may be monitored, column 3 outlines a corresponding sensor used to monitor the parameter, and column 4 relates to the type of physiologic condition or occurrence that may be anticipated using the measurement.

TABLE I

Physiological Parameters to be Sensed or Monitored

| GENERAL MODALITY | SPECIFIC ITEMS | SENSING METHODS | WHAT IT CORRESPONDS TO |
|---|---|---|---|
| Physical Activity | Posture | Gravity direction, accelerometer | Posture |
| | Ambulation/Motion Detector | Piezoelectric Crystal, accelerometer | Motion |
| | Minute Ventilation | Impedence | Respiration (rate and volume) |
| | Temperature | Thermistor | Body temperature |
| | Blood changes with activity | PO2, SA02, pH, Catecholamines, adrenalin | Blood chemistry |
| Cardiac Electrical Activity | Changes in Morphology of Complexes (QRS, T waves) | ECG, Intracardiac Electrogram (EGM), subcutaneous Electrogram (EGM) | Changes in cardiac depolarization or repolarization patterns |
| | Repolarization Alternans, T Wave Alternans, QRS Alternans, ST Segment Alternans | ECG, Intracardiac EGM subcutaneous EGM | Abnormalities on cardiac electrical depolarization, and repolarization |
| | Heart rate & rhythm (NSVT episodes of VT/VF, PVC's heart rate variability) | ECG, Intracardiac EGM subcutaneous EGM | Cardiac rhythms, regularity |
| | Changes in AV Interval, AV Interval variability, dynamic responses of AV interval to changes in HR | ECG, Intracardiac EGM subcutaneous EGM | Cardiac conduction abnormalities, autonomic and paracrine modulation of same |
| | Changes in QT Interval QT Interval variability, Responses of QT Interval to changes in HR | ECG, Intracardiac EGM subcutaneous EGM | Cardiac repolarization autonomic and paracrine modulations of same |
| Cardiac ischemia | ST Segment changes, Q Wave, QRS magnitude And width, | ECG, Intracardiac EGM subcutaneous EGM, blood chemistry (see below) | Mycardial perfusion (balance between supply and demand) |
| Neutral Activity | EEG | Cortical motor strip | Global neutral activity |
| | EMG | Paraspinal muscles | Increases indicate cardiac stress |
| | | Other muscles | |
| | Certain Nerves | Sympathetic | Increases indicate heart stress |
| | | Parasympathetic | Increases indicate relaxation |
| | | Somatic | Correlates to activity |

TABLE I-continued

Physiological Parameters to be Sensed or Monitored

| GENERAL MODALITY | SPECIFIC ITEMS | SENSING METHODS | WHAT IT CORRESPONDS TO |
|---|---|---|---|
| Autonomic Activity | Heart rate variability Baroreflex sensitivity, HR, BP and respiration coupling relationships, Heart rate turbulence | ECG, intracardiac or subcutaneuous EGM, Pressure transducer, Lung Impedance | Autonomic tone, baroreflex, respiratory Sinus arrhythmia |
| Hemodynamic Parameters | Arterial or Venous Pressure | Pressure transducer | Systolic Diastolic and Pulse pressure; central venous pressure |
| | Cardiac chamber pressures | Pressure transducer | Developed pressures, peak systolic, diastolic pressures, dP/dt |
| | Cardiac mechanical activity | Accelerometer, sonomicrometer crystals | Tissue displacement, coordination, contraction |
| Blood Chemistry (central arterial and local tissue and differences between these) | $PO_2$, $SAO_2$ | Oximetry, $O_2$ Probe | Related to cardiac performance |
| | Glucose | Oximetry | Indicator of Myocardial Metabolism |
| | Lactate | Oximetry | Indicators of Myocardial Metabolism |
| | PC $O_2$ | C $O_2$ Probe | Related to cardiac performance |
| | pH | pH Probe | Abnormalities may indicate myocardial electrical instability |
| | Troponin | Molecular Probe | Indicators of Myocardial Ischemia |
| | CKMB | Molecular Probe | Indicators of Myocardial Ischemia |
| | Electrolytes | Molecular Probe | Abnormalities may indicate myocardial electrical instability |
| | Drug levels | Molecular Probe | As indicators of level of protection provided by drug (e.g. antiarrhythmics) |
| | Catecholamines | Molecular Probe | Autonomic Activity/Tone |
| | NO or precursors | Molecular Probe | Related to cardiac injury |
| | Endogenous opiates | Molecular Probe | Autonomic Activity/Tone |
| Time of Day | Clock/Date | Track because activity and risk vary during day or year | |

In one embodiment, electrical stimulation of the spinal cord is performed at locations T1–T12, C1–C8, or other areas of the spinal cord. Any combination of these sites may be stimulated. Such stimulation may involve electrodes implanted near the spine at the desired location. In another embodiment, the vagus and/or peripheral nerve may be stimulated at various locations. If desired, stimulation may be provided subcutaneously, or cutaneously by externally-applied electrodes located in the precordial area or over sites of the pain or any area from which nervous fibers project to the spinal cord at levels T1–T5.

The sites of stimulation may include the following, with any combination being utilized:
   a. Spinal Cord (TI–T12, preferably T1–T4; C1–C8);
   b. Vagus Nerve;
   c. Subcutaneous (precordial, near median nerve, toward muscle);
   d. Peripheral Nerve (median, peritoneal, ulnar, C2 and C3, ansa lenticularis, dorsal root ganglia);
   e. TENS (transcutaneous, in precordial area or over sites of referred pain);
   f. Carotid sinus, and other cranial nerves; and
   g. Sympathetic ganglia.
   h. Intrinsic cardiac neurons Electrical stimulation provide significant benefits when delivered prior to an anticipated cardiac insult, or an event that will induce ischemia. The benefits include minimizing or preventing acute infarct and reducing reperfusion arrhythmia. In one embodiment, the therapy is delivered thirty minutes or more prior to the anticipated on-set of an insult such as ischemia. As much as possible, the above therapies should be implemented prior to the insult using one or more of the following embodiments illustrated in the flowcharts of FIGS. 5A through 5E.

Figure 6A:
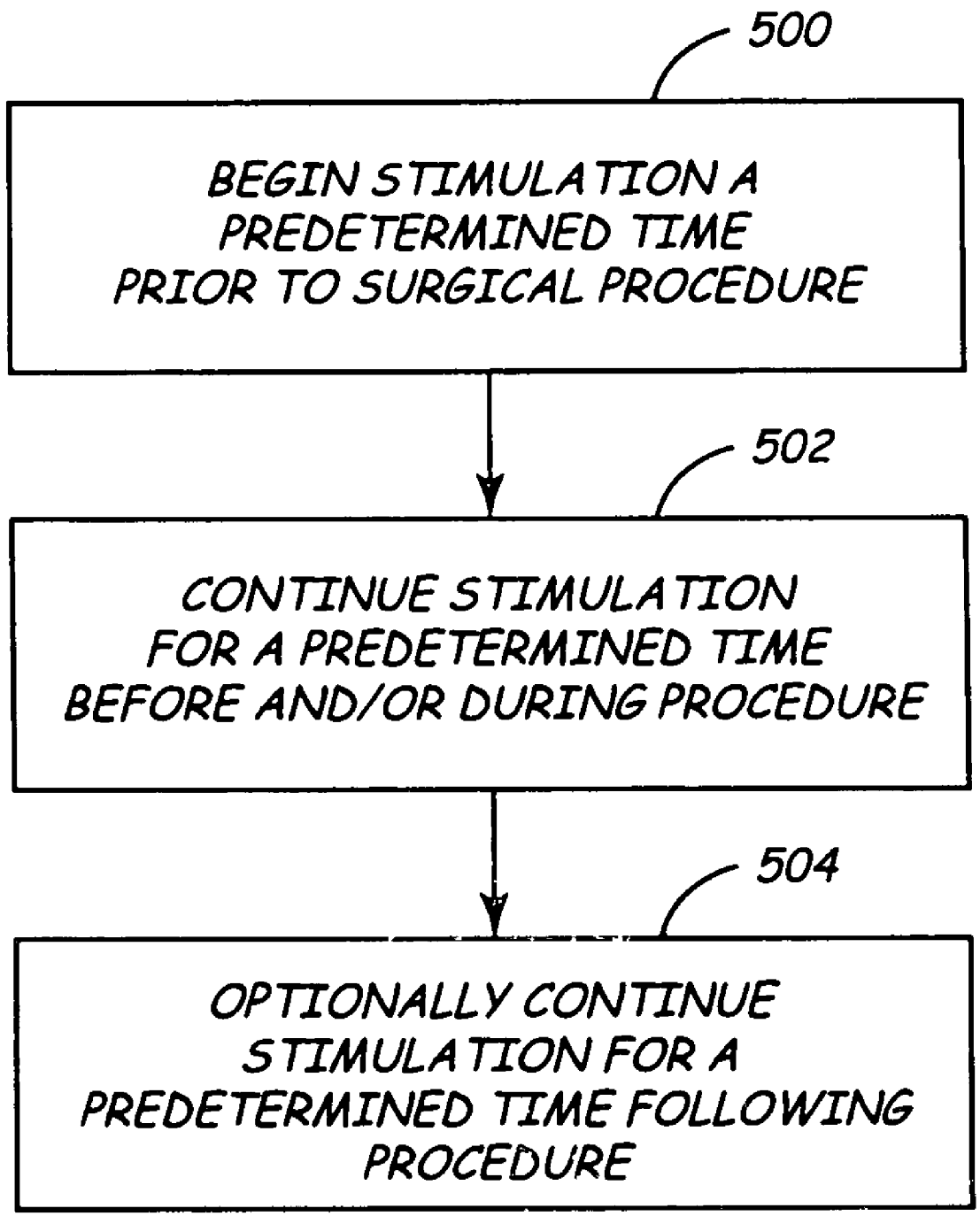
FIG. 6A is a flowchart illustrating delivery of stimulation prior to planned cardiac interventions, like bypasses, angioplasties or stents procedures.

FIG. 6A is a flowchart illustrating delivery of stimulation prior to planned cardiac interventions, like bypasses, angioplasties or stents (block 500). The stimulation could be applied for a predetermined time such as 30–120 minutes prior to the intervention (block 502). Stimulation may be continued for hours or days after the procedure to minimize adverse effects or to increase or even maximize patency of vessels (block 504).

Figure 6B:
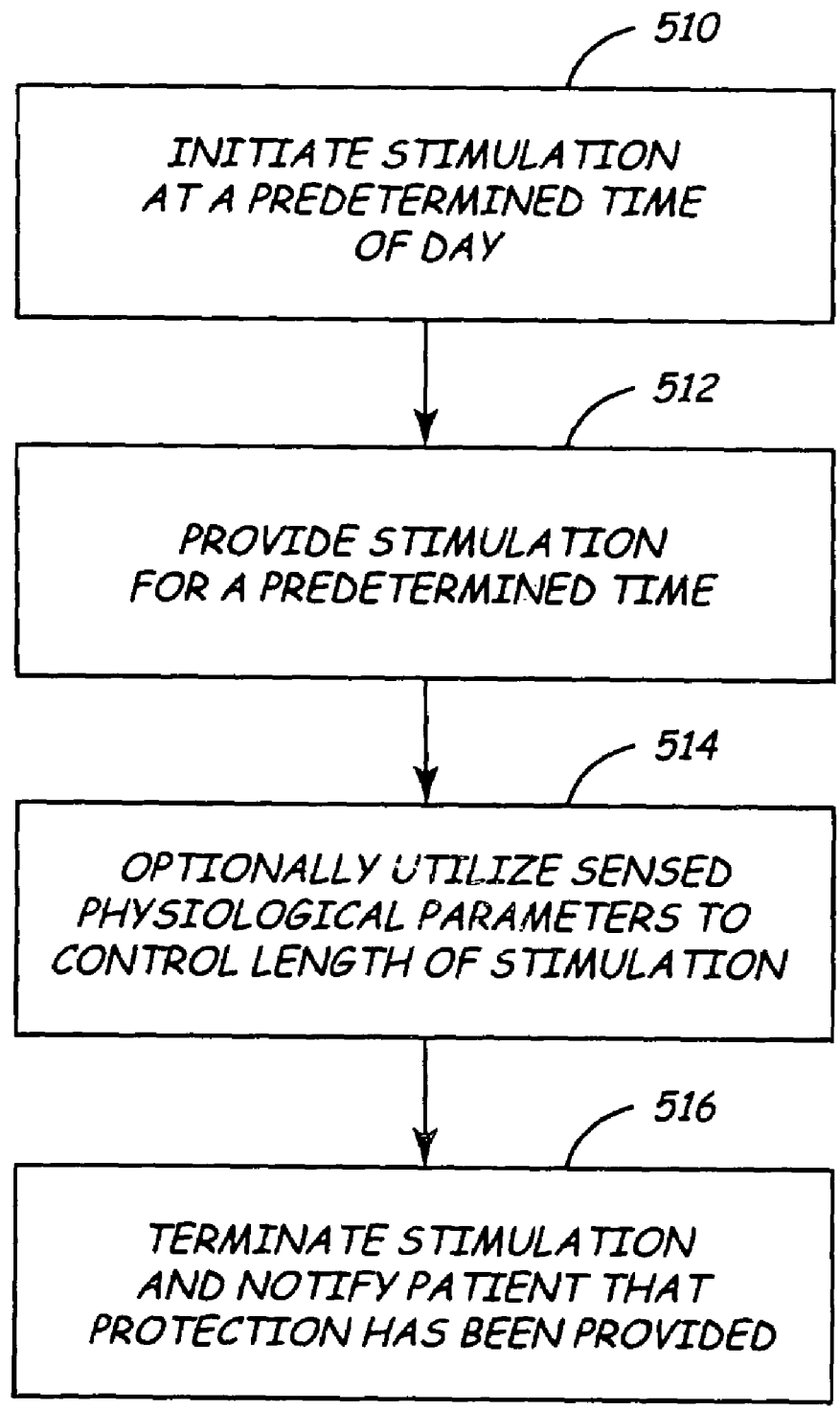
FIG. 6B is a flowchart illustrating delivery of stimulation at a particular time of day.

FIG. 6B is a flowchart illustrating delivery of stimulation at a particular time of day (block 510). For example, stimulation may be provided when a patient wakes up in the morning. A timer may be utilized to initiate subthreshold stimulation, or alternatively, to initiate suprathreshold stimulation to provide paresthesia. After a predetermined time such as thirty minutes (block 512), or when sensed physiological parameters indicate that the appropriate level of cardiovascular protection has been established (block 514), the patient can be alerted (516). This could be accomplished, for example, by use of stimulation producing a stronger paresthesia.

Figure 6C:
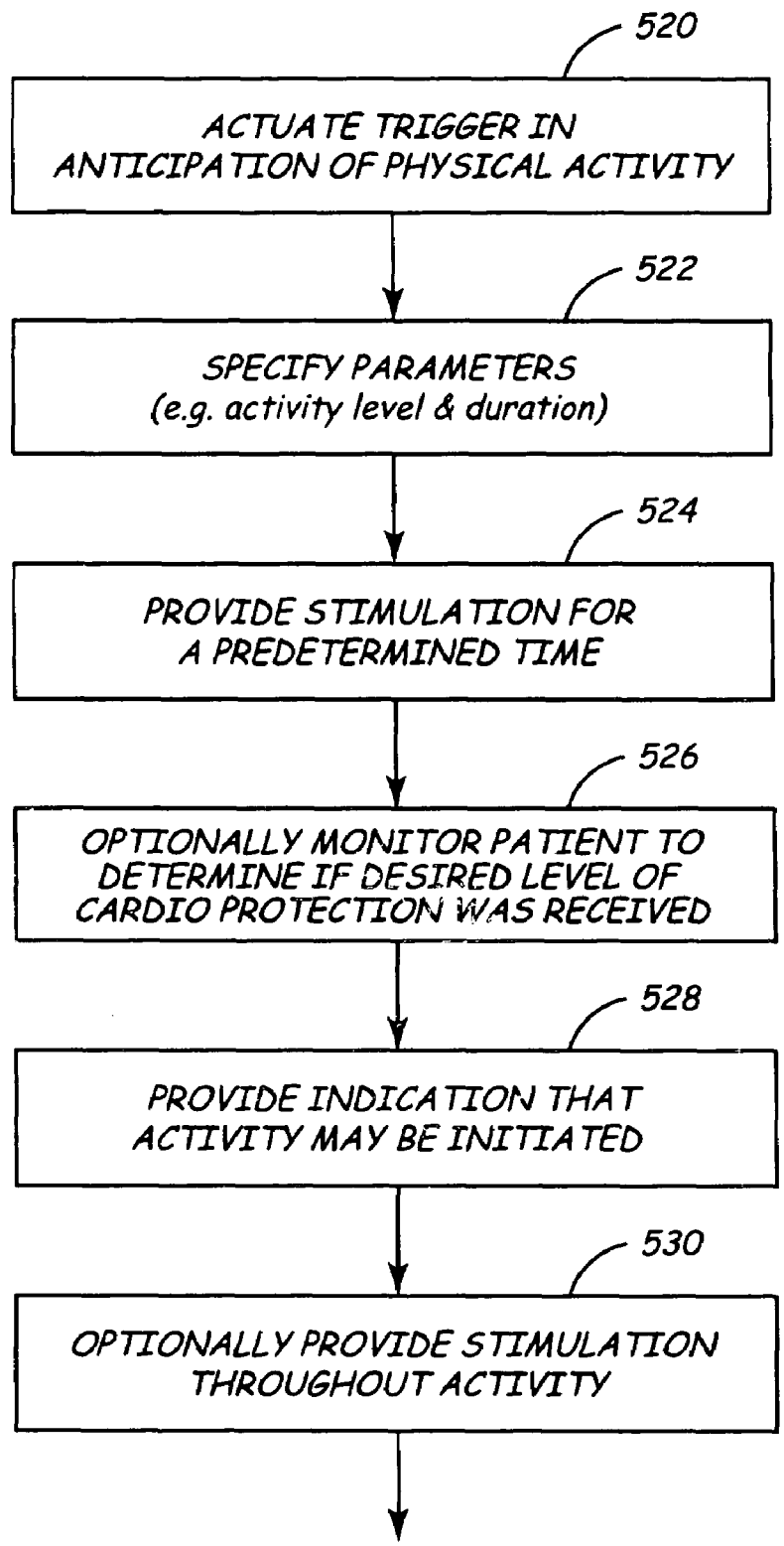
FIG. 6C is a flowchart illustrating delivery of stimulation initiated because a patient anticipates physical activity and manually triggers therapy.

FIG. 6C is a flowchart illustrating delivery of stimulation initiated because a patient anticipates physical activity and manually triggers therapy (block 520). This may be accomplished using an externally-positioned magnet as may be used to close a reed switch. Alternatively, a tapping sequence may be initiated as is known in the art. In this embodiment, the patient performs a tapping action over the implanted device as may be accomplished using a finger. This tapping action is detected by an accelerometer or similar sensor within the device so that therapy may be initiated.

In one embodiment, an expected intensity of the activity or other optional parameters may also be specified (block 522). After stimulation has been delivery for the specified time (block 524) and/or after the appropriate level of cardio protection has been determined to have been established (block 526), the device provides an indication that activity may be initiated (block 528). Stimulation may continue throughout the activity, if desired (block 530).

Figure 6D:
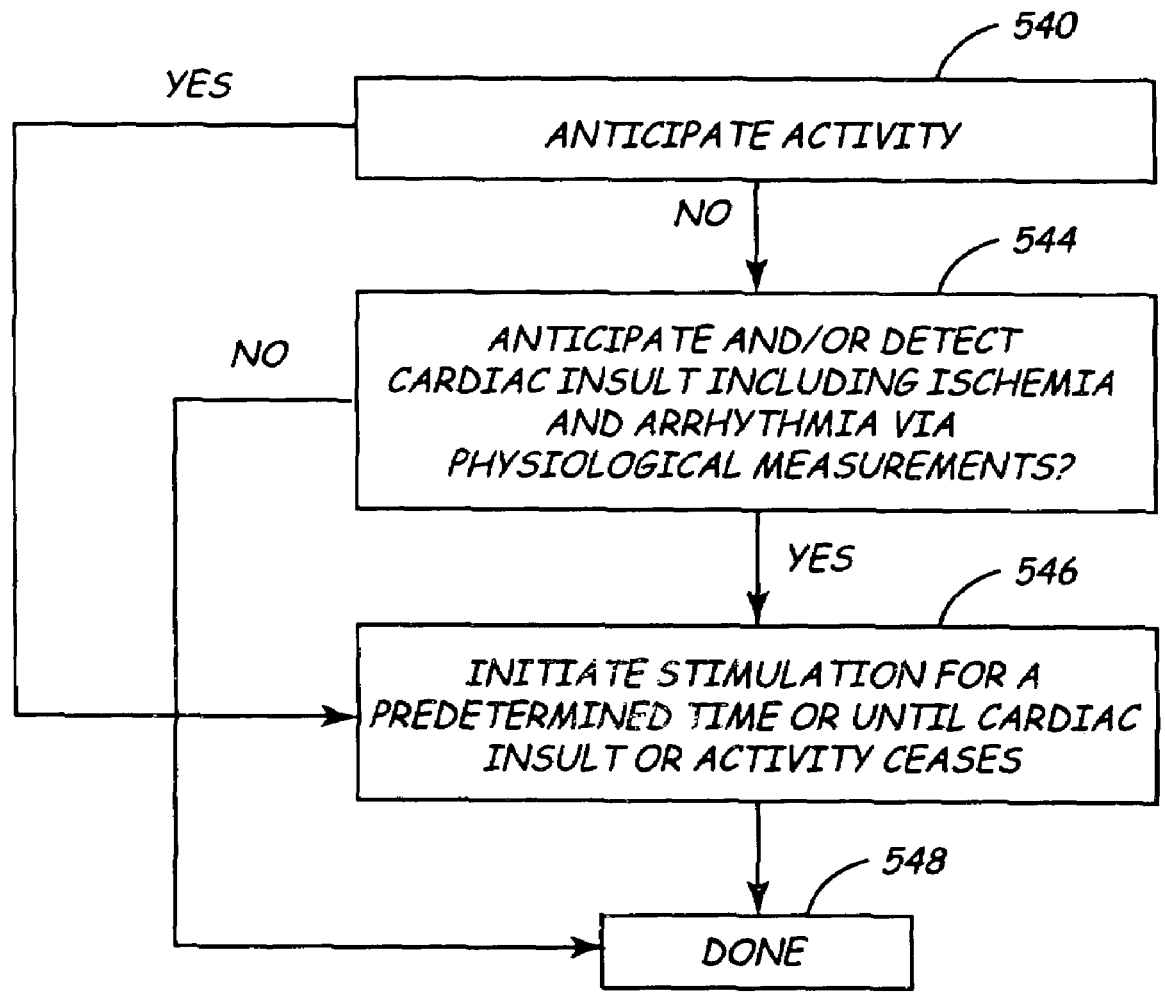
FIG. 6D is a flowchart illustrating stimulation initiated at the first signs of activity in an anticipatory manner, or at the first indication that an insult may be predicted.

FIG. 6D is a flowchart illustrating stimulation initiated at the first signs of activity in an anticipatory manner (block 540), or at the first indication that ischemia, an episode of malignant ventricular arrhythmia, and/or any of the other insults discussed above may be anticipated (block 544). This type of indication may be detected by one or more of the sensing mechanisms discussed above.

Figure 6E:
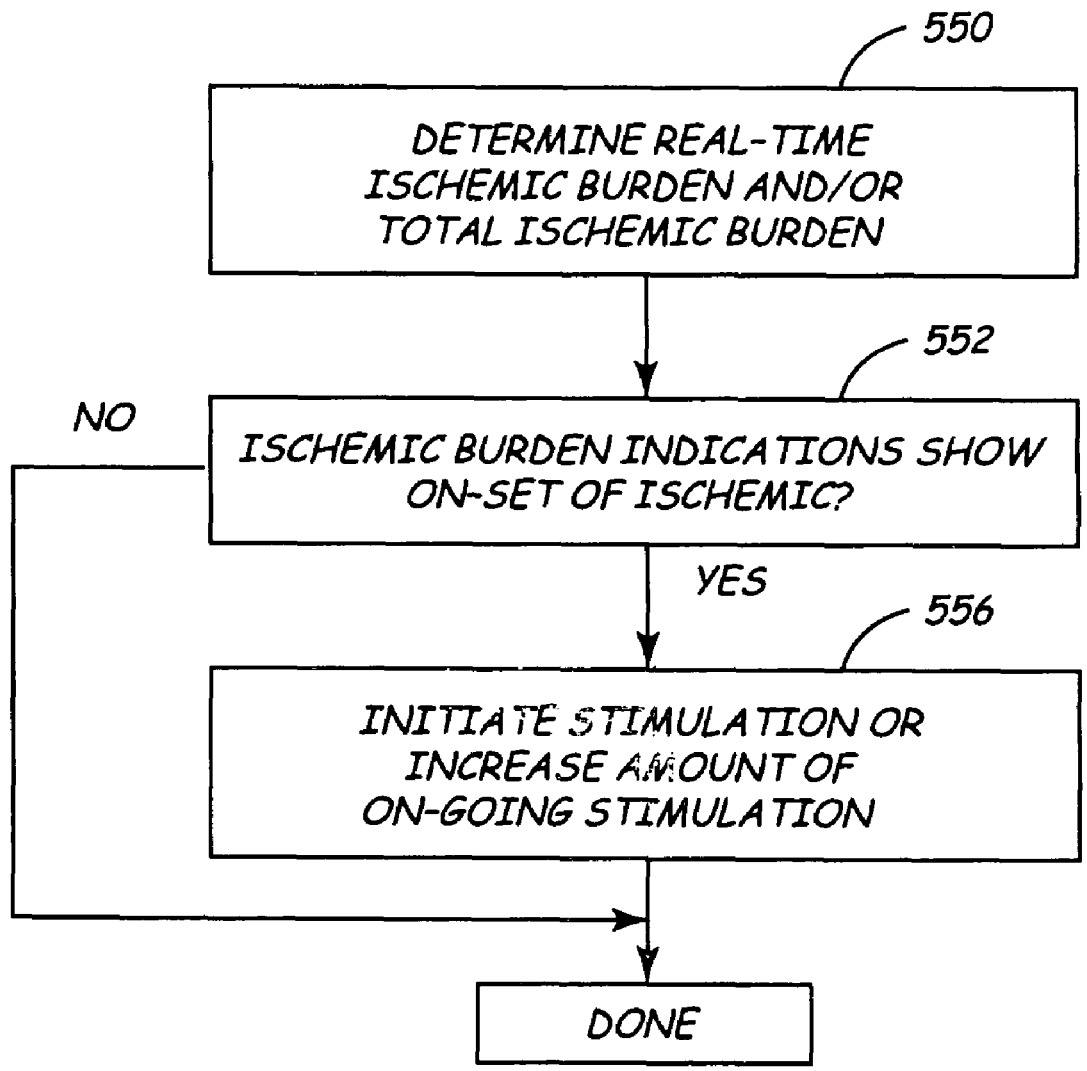
FIG. 6E is a flowchart illustrating stimulation initiated based on a real time recording of ischemic burden and total ischemic burden.

FIG. 6E is a flowchart illustrating stimulation initiated based on a real time recording of ischemic burden and total ischemic burden (blocks 550 and 552). If desired, the prophylactic amount of stimulation could be increased if these measurements show increased ischemia in general, or an increased likelihood of the onset of ischemia (block 556).

Figure 6F:
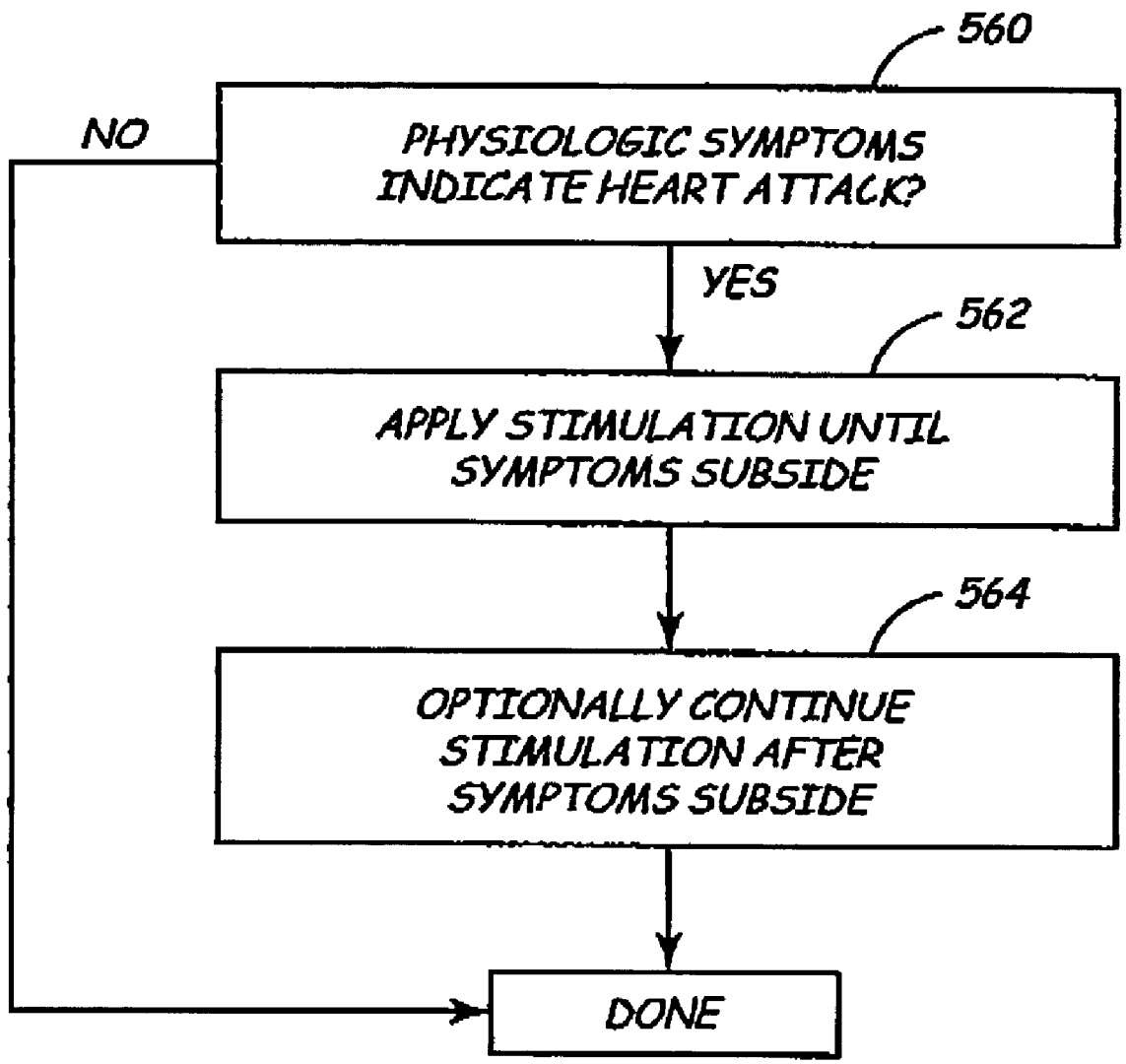
FIG. 6F illustrates the delivery of the therapy for protection during a suspected heart attack.

FIG. 6F illustrates the delivery of the therapy for protection during a suspected heart attack. To promote optimal recovery, stimulation may be applied by healthcare professionals as soon as possible in an appropriate form if a heart attack is even suspected (blocks 560 and 562). This is done using subcutaneous or cutaneous electrode systems discussed above. This stimulation may continue after the symptoms subside to further protect the cardiac tissue (564).

Table II illustrates some of the benefits associated with the electrical stimulation provided by the current invention, and includes sites of stimulation for achieving these benefits. Table II further lists one or more physiological parameters that may be monitored when delivering stimulation to achieve a desired effect.

TABLE II

Benefits of Stimulation

| BENEFITS | OPTIMAL SITES FOR STIMULATION | PHYSIOLOGICAL PARAMETERS TRACKED |
|---|---|---|
| Prevention of VT/VF Incidents | Vagal activation or sympathetic reduction, SCS | Cardiac electrical, Cardiac Ischemia, Autonomic Activity, Physical Activity, Heart Rate and Rhythm |
| Reduce PVC's | Vagal activation or sympathetic reduction, SCS | Cardiac electrical, Cardiac Ischemia, Autonomic Activity, Physical Activity, Heart Rate and Rhythm |
| Reduce NSVT | Vagal activation or sympathetic reduction, SCS | Cardiac electrical, Cardiac Ischemia, Autonomic Activity, Physical Activity, Heart Rate and Rhythm |
| Lessen Cardiac Ischemia | Vagal activation or sympathetic reduction, SCS | Cardiac Ischemia; total ischemic burden, Physical Activity |
| Reduce Angina | Vagal activation or sympathetic reduction, SCS | Physical Activity, Cardiac Ishemia |
| Improved Exercise Tolerance | Vagal activation or sympathetic reduction, SCS | Physical Activity, respiration, blood chemistry |
| Rebalance Autonomic System | Vagal activation or sympathetic reduction, SCS | Cardiac electrical, Autonomic Activity, Hemodynamics |
| Improve Cardiac Performance: pump function, preload/afterload | Vagal activation or sympathetic reduction, SCS | Cardiac electrical and hemodynamics |
| Improve Cardiac Paracrine Function or Balance | Vagal activation or sympathetic reduction, SCS | Cardiac electrical and hemodynamics |
| Alter AV electrical function | Vagal activation or sympathetic reduction, SCS | Cardiac electrical |
| Restore heart rate Variability | Vagal activation or sympathetic reduction, SCS | Cardiac electrical, Autonomic Activity |
| Other | Vagal activation or sympathetic reduction, SCS | |

The above-described closed-loop system may combine electrical stimulation with conventional drug therapy. The drug therapy may be provided by an implanted delivery device such as that discussed above, for example. The closed-loop system may be utilized to titrate the drug delivery and the stimulation in much the same manner as discussed above in conjunction with the closed loop electrical stimulation.

As noted above, the inventive system and method provides a mechanism for employing closed-loop controls to initiate and deliver electrical stimulation. As shown in FIG. 3, the system may also provide the ability for the patient to activate the stimulation based on the onset of a physical condition such as exertion or pain. This patient-initiated therapy may be limited or controlled by a programmable feature as specified by a physician. A timer may also be provided to initiate and control therapy at one or more times during the day.

In one embodiment, a notification feature is provided to notify the patient and/or a physician of changing patient conditions indicative of increased ischemic risk. The invention may further include means to discontinue or limit therapy when closed-loop feedback techniques are leading to an undesirable situation.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and

The invention claimed is:

1. A system to perform closed loop controlled delivery of electrical stimulation to excitable neural tissue of a portion of the spine of a body, comprising:
a sensing circuit to sense at least one physiologic parameter and provide an output signal related thereto, wherein said sensing circuit operatively couples to a sensor adapted to sense a change in paraspinal muscle tone;
a stimulation circuit to provide the electrical stimulation to excitable neural tissue of a portion of the spine in response to the output signal;
a drug dispensing apparatus coupled to a catheter and adapted to deliver biologically-active agents via the catheter to the body; and
a closed loop control circuit coupled to the sensing circuit, to the stimulation circuit, and to the drug dispensing apparatus configured to control the stimulation circuit and the drug dispensing apparatus based on anticipation of an occurrence of a cardiac insult as indicated by the at least one physiologic parameter, wherein at least one input to said closed loop control circuit includes the output signal from said sensing circuit.

2. The system of claim 1, wherein the control circuit includes a patient-activation mechanism.

3. The system of claim 1, wherein the control circuit includes means for initiating the electrical stimulation in response to the at least one physiologic parameter sensed by the sensing circuit, and said at least one physiologic parameter comprises an increase in the muscle tone of the paraspinal muscles.

4. The system of claim 1, wherein the control circuit includes means for altering the electrical stimulation provided in response to the at least one physiologic parameter sensed by the sensing circuit.

5. The system of claim 1, wherein the control circuit includes means for ceasing the electrical stimulation provided in response to the at least one physiologic parameter sensed by the sensing circuit.

6. The system of claim 3, and further including means for notifying a patient of the anticipation of the occurrence of the cardiac insult.

7. The system of claim 1, wherein the stimulation circuit includes at least one implanted electrode.

8. The system of claim 1, wherein the stimulation circuit includes at least one subcutaneous electrode.

9. The system of claim 1, wherein the stimulation circuit includes at least one electrode positioned proximate an external surface of the body.

10. The system of claim 1, and further including a storage device coupled to the control circuit to store results of past electrical stimulation; and
wherein the control circuit include means for performing future electrical stimulation based on the results of past electrical stimulation.

11. The system of claim 3, and further including a drug delivery system coupled to the control circuit to deliver biologically-active agents based on the anticipation of the occurrence of the cardiac insult.

12. A device to provide electrical stimulation to at least one predetermined portion of excitable neural tissue of a portion of the spine of a patient, comprising:
means for sensing at least one physiologic indication in the patient's body which relates to a probable future cardiac insult event, wherein said means for sensing comprises a sensor adapted to sense a change in paraspinal muscle tone;
means for providing stimulation to the at least one predetermined portion of excitable neural tissue of a portion of the spine of a patient;
means for dispensing a biologically-active substance to the patient; and
means for performing closed loop control of the stimulation means and the means for dispensing to provide the stimulation and administer the biologically-active substance based on an indication of the probable future cardiac insult event as determined by the physiologic indication.

13. An apparatus for protecting cardiac tissue from insult, comprising:
at least one electrode positionable at a region adjacent a portion of excitable neural tissue of a portion of the spine of a patient;
a sensing circuit to detect at least one physiologic parameter and provide an output signal related thereto, wherein said sensing circuit comprises a sensor adapted to sense a change in paraspinal muscle tone;
a drug dispenser including a catheter adapted to dispense a biologically-active substance to the patient; and
a controller adapted to deliver closed loop-controlled of at least one of an electrical stimulation therapy to the at least one electrode for a period of time prior to onset of a cardiac insult and delivery of the biologically-active substance, wherein at least one parameter of the electrical stimulation therapy and the delivery of the biologically-active substance is controlled as a function of the output signal related to the sensed physiologic parameter.

14. The apparatus of claim 13, wherein the controller includes means for delivering electrical stimulation for a period of time after the onset of the insult.

15. The apparatus of claim 14, wherein the controller includes means for delivering electrical stimulation for a period of time after the termination of the insult.

16. The apparatus of claim 13, and further including a circuit coupled to the controller to provide electrical stimulation to cardiac tissue.

17. The apparatus of claim 16, wherein the electrical stimulation comprises pacing pulses.

* * * * *